US010206876B2

(12) United States Patent
Amselem et al.

(10) Patent No.: US 10,206,876 B2
(45) Date of Patent: *Feb. 19, 2019

(54) DEPOT FORMULATIONS OF A LOCAL ANESTHETIC AND METHODS FOR PREPARATION THEREOF

(71) Applicant: PAINREFORM LTD., Herzlia Pituah (IL)

(72) Inventors: Shimon Amselem, Rehovot (IL); Michael Naveh, Ramat Hasharon (IL)

(73) Assignee: PAINREFORM LTD., Herzlia Pituah (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/584,391

(22) Filed: May 2, 2017

(65) Prior Publication Data

US 2018/0049985 A1 Feb. 22, 2018

Related U.S. Application Data

(63) Continuation of application No. 14/399,815, filed as application No. PCT/IL2013/050410 on May 9, 2013, now Pat. No. 9,668,974.

(60) Provisional application No. 61/645,066, filed on May 10, 2012, provisional application No. 61/649,400, filed on May 21, 2012, provisional application No. 61/781,625, filed on Mar. 14, 2013, provisional application No. 61/781,595, filed on Mar. 14, 2013.

(51) Int. Cl.

| A61K 47/10 | (2017.01) |
| A61K 9/127 | (2006.01) |
| A61K 47/20 | (2006.01) |
| A61K 47/24 | (2006.01) |
| A61K 47/44 | (2017.01) |
| A61K 31/192 | (2006.01) |
| A61K 31/196 | (2006.01) |
| A61K 31/445 | (2006.01) |
| A61K 31/573 | (2006.01) |
| A61K 9/00 | (2006.01) |

(52) U.S. Cl.
CPC .......... *A61K 9/1277* (2013.01); *A61K 9/0024* (2013.01); *A61K 9/127* (2013.01); *A61K 31/192* (2013.01); *A61K 31/196* (2013.01); *A61K 31/445* (2013.01); *A61K 31/573* (2013.01); *A61K 47/10* (2013.01); *A61K 47/20* (2013.01); *A61K 47/24* (2013.01); *A61K 47/44* (2013.01)

(58) Field of Classification Search
None
See application file for complete search history.

(56) References Cited

U.S. PATENT DOCUMENTS

| 4,252,793 | A | | 2/1981 | Altman |
| 5,004,611 | A | | 4/1991 | Leigh |
| 5,173,219 | A | | 12/1992 | Kim |
| 5,422,120 | A | | 6/1995 | Kim |
| 5,455,044 | A | | 10/1995 | Kim et al. |
| 5,480,656 | A | | 1/1996 | Okada et al. |
| 5,538,739 | A | | 7/1996 | Bodmer et al. |
| 5,576,017 | A | | 11/1996 | Kim |
| 5,576,018 | A | | 11/1996 | Kim |
| 5,635,206 | A | | 6/1997 | Ganter |
| 5,654,010 | A | | 8/1997 | Johnson et al. |
| 5,660,854 | A | | 8/1997 | Haynes et al. |
| 5,693,337 | A | | 12/1997 | Suzuki et al. |
| 5,723,147 | A | | 3/1998 | Kim et al. |
| 5,744,337 | A | | 4/1998 | Price et al. |
| 5,759,573 | A | | 6/1998 | Kim |
| 5,766,627 | A | | 6/1998 | Sankaram et al. |
| 5,807,572 | A | | 9/1998 | Kim et al. |
| 5,834,489 | A | * | 11/1998 | Eek ................ A61K 31/445 514/330 |
| 5,863,549 | A | | 1/1999 | Tarantino |
| 5,891,467 | A | | 4/1999 | Willis |
| 5,922,340 | A | | 7/1999 | Berde et al. |
| 5,931,809 | A | | 8/1999 | Gruber et al. |
| 5,955,504 | A | | 9/1999 | Wechter et al. |
| 5,962,016 | A | | 10/1999 | Willis |
| 5,981,592 | A | | 11/1999 | Wechter et al. |
| 5,993,850 | A | | 11/1999 | Sankaram et al. |
| 5,997,899 | A | | 12/1999 | Ye et al. |
| 6,008,256 | A | | 12/1999 | Haraguchi et al. |
| 6,045,824 | A | | 4/2000 | Kim et al. |
| 6,071,534 | A | | 6/2000 | Kim et al. |
| 6,106,858 | A | | 8/2000 | Ye et al. |

(Continued)

FOREIGN PATENT DOCUMENTS

| CN | 1823732 A | 8/2006 |
| CN | 1823734 A | 8/2006 |

(Continued)

OTHER PUBLICATIONS

Matsuki and Kaneshina (2006) Thermodynamics of Bilayer Phase Transitions of Phospholipids. Netsu Sokutei (2006) Temperature Measurement 33(2): 74-82, abstract.

Fiume, "Final report on the safety assessment of Lecithin and Hydrogenated Lecithin", International Journal of Toxicology, vol. 20, 2001: pp. 21-45.

Kanai et al., "Comparisons of the anesthetic potency and intracellular concentrations of S(−) and R( +) bupivacaine and ropivacaine in crayfish giant axon in vitro", Anesth Analg, vol. 90, 2000: pp. 415-420.

Mazoit et al., "Binding of long-lasting local anesthetics to lipid emulsions", Anesthesiology, vol. 110, 2009: pp. 380-386.

(Continued)

*Primary Examiner* — Isaac Shomer
(74) *Attorney, Agent, or Firm* — Rothwell, Figg, Ernst & Manbeck, P.C.

(57) ABSTRACT

The invention provides extended release pro-liposomal, non-aqueous, pharmaceutical formulations of a local anesthetic in the form of a clear oily solution and methods for making same. The formulations can be administered by infiltration into an incision, or by injection.

24 Claims, 5 Drawing Sheets

(56) References Cited

U.S. PATENT DOCUMENTS

| | | |
|---|---|---|
| 6,132,766 A | 10/2000 | Sankaram et al. |
| 6,160,018 A | 12/2000 | Wechter et al. |
| 6,171,613 B1 | 1/2001 | Ye et al. |
| 6,193,998 B1 | 2/2001 | Ye et al. |
| 6,241,999 B1 | 6/2001 | Ye et al. |
| 6,277,413 B1 | 8/2001 | Sankaram |
| 6,306,432 B1 | 10/2001 | Shirley et al. |
| 6,326,020 B1 * | 12/2001 | Kohane .............. A61K 31/135 424/426 |
| 6,428,529 B1 | 8/2002 | Gruber et al. |
| 6,569,463 B2 | 5/2003 | Patel et al. |
| 6,599,527 B1 | 7/2003 | Leigh et al. |
| 6,861,064 B1 | 3/2005 | Laakso et al. |
| 7,074,826 B2 | 7/2006 | Wechter et al. |
| 7,229,630 B2 | 6/2007 | Chen et al. |
| 7,387,791 B2 | 6/2008 | Betageri et al. |
| 7,547,452 B2 | 6/2009 | Atkins et al. |
| 7,569,230 B2 | 8/2009 | Chen et al. |
| 7,575,757 B2 | 8/2009 | Chen et al. |
| 7,871,632 B2 | 1/2011 | Chen |
| 7,968,122 B2 | 6/2011 | Chen |
| 8,026,250 B2 | 9/2011 | Chen |
| 8,182,835 B2 | 5/2012 | Kim et al. |
| 8,221,792 B2 | 7/2012 | Chen et al. |
| 8,222,268 B2 | 7/2012 | Chen |
| 8,236,292 B2 | 8/2012 | Thuresson et al. |
| 8,313,766 B2 | 11/2012 | Chen et al. |
| 9,668,974 B2 * | 6/2017 | Amselem .............. A61K 47/10 |
| 9,849,088 B2 * | 12/2017 | Amselem .............. A61K 47/10 |
| 2002/0136759 A1 | 9/2002 | Szebeni et al. |
| 2003/0068364 A1 | 4/2003 | Garces et al. |
| 2003/0099674 A1 | 5/2003 | Chen |
| 2003/0191093 A1 | 10/2003 | Chen et al. |
| 2003/0236306 A1 | 12/2003 | Chen et al. |
| 2005/0020546 A1 | 1/2005 | Laidlaw et al. |
| 2005/0026877 A1 | 2/2005 | Chen et al. |
| 2005/0049209 A1 | 3/2005 | Chen |
| 2005/0186230 A1 | 8/2005 | Chen |
| 2005/0287180 A1 | 12/2005 | Chen |
| 2006/0014730 A1 | 1/2006 | Ulm et al. |
| 2006/0024360 A1 | 2/2006 | Chen |
| 2006/0067952 A1 | 3/2006 | Chen |
| 2006/0078606 A1 | 4/2006 | Kim et al. |
| 2006/0148891 A1 | 7/2006 | Ternansky et al. |
| 2006/0189586 A1 | 8/2006 | Cleland |
| 2007/0003614 A1 | 1/2007 | Chen et al. |
| 2007/0004688 A1 | 1/2007 | Laidlaw et al. |
| 2007/0078434 A1 | 4/2007 | Keusch et al. |
| 2007/0207173 A1 | 9/2007 | Chen |
| 2007/0235889 A1 | 10/2007 | Hartounian et al. |
| 2008/0220079 A1 | 9/2008 | Chen et al. |
| 2009/0017105 A1 | 1/2009 | Khattar et al. |
| 2009/0221594 A1 | 9/2009 | Chen et al. |
| 2010/0041704 A1 | 2/2010 | Aberg et al. |
| 2010/0062988 A1 | 3/2010 | Chen et al. |
| 2010/0178329 A1 | 7/2010 | Gaal et al. |
| 2010/0305030 A1 | 12/2010 | Couvreur et al. |
| 2010/0305500 A1 | 12/2010 | Lambert et al. |
| 2010/0310661 A1 | 12/2010 | Chen et al. |
| 2011/0223259 A1 | 9/2011 | Chen |
| 2011/0237536 A1 | 9/2011 | Didsbury et al. |
| 2011/0250264 A1 | 10/2011 | Schutt et al. |
| 2011/0280932 A1 | 11/2011 | Garcia et al. |
| 2012/0016020 A1 | 1/2012 | Chen et al. |
| 2012/0046220 A1 | 2/2012 | Chen et al. |
| 2012/0114740 A1 | 5/2012 | Garcia et al. |
| 2012/0225118 A1 | 9/2012 | Chen et al. |
| 2012/0231070 A1 | 9/2012 | Kim et al. |
| 2012/0316108 A1 | 12/2012 | Chen et al. |

FOREIGN PATENT DOCUMENTS

| | | | |
|---|---|---|---|
| CN | 101002771 A | 7/2007 | |
| EP | 0770387 A1 | 5/1997 | |
| EP | 0282405 | 7/1998 | |
| EP | 2243495 A1 | 10/2010 | |
| JP | 2002-513748 | 5/2002 | |
| JP | 3571717 B2 | 9/2004 | |
| JP | 2007-511525 | 5/2007 | |
| JP | 2008-501676 | 1/2008 | |
| JP | 2008-502690 | 1/2008 | |
| RU | 2152215 | 7/2000 | |
| RU | 2159106 | 11/2000 | |
| RU | 2429242 | 9/2011 | |
| WO | 89/00077 | 1/1989 | |
| WO | 93/19736 | 10/1993 | |
| WO | WO-9319736 A1 * | 10/1993 | ........... A61K 9/1271 |
| WO | 94/08623 | 4/1994 | |
| WO | 94/23697 | 10/1994 | |
| WO | 95/13796 | 5/1995 | |
| WO | 96/08235 | 3/1996 | |
| WO | 98/14171 | 4/1998 | |
| WO | 98/33483 | 8/1998 | |
| WO | 99/12523 | 3/1999 | |
| WO | 99/13865 | 3/1999 | |
| WO | 99/25319 | 5/1999 | |
| WO | 00/03660 | 1/2000 | |
| WO | 00/59482 | 10/2000 | |
| WO | 00/74653 | 12/2000 | |
| WO | 01/19403 | 3/2001 | |
| WO | 02/32395 | 4/2002 | |
| WO | 02/96368 | 12/2002 | |
| WO | 2006/002050 | 1/2006 | |
| WO | 2008/138089 | 11/2008 | |
| WO | 2010/138918 | 12/2010 | |
| WO | 2011/075623 | 6/2011 | |
| WO | 2011075353 | 6/2011 | |
| WO | 2011/121034 | 10/2011 | |
| WO | 2011/127456 | 10/2011 | |
| WO | 2011/153513 | 12/2011 | |
| WO | 2012/006081 | 1/2012 | |
| WO | 2012/037311 A1 | 3/2012 | |
| WO | 2012/054447 | 4/2012 | |
| WO | 2012/058483 | 5/2012 | |
| WO | 2012/170796 | 12/2012 | |

OTHER PUBLICATIONS

Strickley, "Solubilizing Excipients in Oral and Injectable Formulations", Pharmaceutical Research, vol. 21 (2), Feb. 2004: pp. 201-230.

Wang et al., "Lyophilization of water-in-oil emulsions to prepare phospholipid-based anhydrous reverse micelles for oral peptide delivery", European Jouran of Pharmaceutical Sciences, vol. 39, 2010: pp. 373-379.

Yang et al., "On the stability of liposomes and catansomes in aqueous alcohol solutions", Langmuir 24, 2008: pp. 1695-1700.

Sato, Koichi On ripple structure of phospholipid membrane (lecture, "Physics of membrane"); Physical Studies (1997) 68(3): 262-265; English summary.

* cited by examiner

DEPOT FORMULATIONS OF A LOCAL ANESTHETIC AND METHODS FOR PREPARATION THEREOF

FIELD OF THE INVENTION

The present invention relates generally to a depot formulation that can be injected or infiltrated into a desired location and which can provide sustained release for a local anesthetic agent. Specifically, the present invention relates to a non-aqueous pro-liposomal depot formulation essentially devoid of synthetic lipids, which advantageously create liposomes or other lipidic vesicular structures in situ upon contact with body fluids.

BACKGROUND OF THE INVENTION

Post-Operative Pain (POP), also referred to as post-surgical pain, is a poorly understood syndrome following surgical procedures. POP is a complex response to tissue trauma during surgery that stimulates hypersensitivity of the central nervous system. The result is pain in areas not directly affected by the surgical procedure. Post-operative pain may be experienced by an inpatient or outpatient. It can be felt after any surgical procedure, whether it is minor dental surgery or a triple-bypass heart operation.

POP reduction is currently maintained by injecting short duration local anesthetics to the surgical wound, by the use of a local anesthetic delivery system (pumps) to the wound and by per os self-administration of pain relievers, mainly opiate based. It is desirable to prolong the effect and duration of the local anesthetics, thus to reduce the need for opiate-based analgesia post-surgery. Post-operative analgesic therapy with opiate based or NSAID can result in significant post-surgical complications, and may cause the patient to be substantially compromised with regards to gastrointestinal, respiratory, and cognitive functions.

Use of an extended release local anesthetic formulation can improve patients' well-being and expedite recovery, assist in patient compliance, reduce hospital stays and hospital costs and, therefore, result in cost savings to the patient and the healthcare system. The market for such extended release local anesthetics is expected to exceed several hundred million dollars annually in the U.S. alone.

There is a real need for providing different approaches to post-surgical pain management. A variety of interventions may be used before, during, and after surgery. Most of these methods involve medications given orally, intravenously, intramuscularly, or topically (via the skin). Some must be administered by a health care professional, others by self-administration by the patient.

Currently, post-surgical pain is managed by the administration of narcotics and analgesics immediately after surgery. These drugs are given by intravenous or intramuscular injection, or taken by mouth. Utilization of these drugs, nevertheless, has variant applications, while some hospitals insist on a routine of scheduled medications, other are giving medications only as needed.

Some hospitals advocate continuous, around-the-clock dosing via an injection pump-type dosing device that delivers medication into the veins (intravenously, the most common method), under the skin (subcutaneously), or between the dura mater and the backbone (epidurally). A health care provider programs the device for dosage and minimal intervals while delivery is controlled by the patient. Total permitted dosage during the time for which the device is set (commonly 8 hours, sometimes 12) is pre-programmed. The patient administers the dose by pushing a button, and is encouraged to keep a steady supply of medication within his or her system when pain increases. This is called patient-controlled analgesia (PCA).

PCA provides pain medication according to the patient's need. However, because opiate-like pain-relievers are the medications these pumps deliver, there has been some concern about possible narcotic addiction.

A useful method, by which long lasting post-operative analgesia can be achieved, is by a single application of a depot formulation. The depot can be optimized for injection, infiltration into an incision, implantation or topical application. In a depot formulation, a therapeutic agent is formulated with carriers providing a gradual release of the therapeutic agent over a period of several hours to several days, or longer. Depot formulations are generally based upon a biodegradable matrix which gradually undergoes degradation or disperses thus releasing the therapeutic agent.

Hence, the advantage of depot formulations is that active therapeutic agents are released gradually over long periods without the need for repeated dosing. These formulations are thus highly suitable for situations where patient compliance is difficult, unreliable or where a level dosage is highly important, such as with formulations of mood-altering active therapeutic agents, active therapeutic agents with a narrow therapeutic window, and active therapeutic agents administered to children or other patients whose lifestyle is incompatible with a reliable dosing regimen. Particular classes of active therapeutic agents for which this aspect offers an advantage include contraceptives, hormones (including contraceptive hormones, and hormones used in children such as growth hormone), antibiotics, anti-addictive agents, supplements such as vitamin or mineral supplements, anti-depressants, local anesthetics, pain relieving medications, and anticonvulsants.

Many depot formulations rely on particles incorporated into liposomes or microspheres for encapsulation of the therapeutic agent. Liposomal depot formulations, however, are difficult to manufacture, are extremely sensitive to surface active agents, have limited shelf-life or require a sub-ambient temperature for storage. Due to their particle size and fragile nature which prevents the use of common sterilization methods such as filtration, irradiation or autoclaving, liposomal multivesicular depot formulations are usually made under aseptic conditions which make the manufacturing process cumbersome and costly. In addition, liposomal depot formulations generally provide extended release of the therapeutic agent for up to 12 hours only. Various products are described with drugs incorporated into microspheres in oil based carriers. For example U.S. Pat. No. 6,132,766 to Sankaram et al. discloses a multivesicular liposome composition containing at least one acid other than a hydrohalic acid and at least one biologically active substance, the vesicles having defined size distribution, adjustable average size, internal chamber size and number, and provides a controlled release rate of the biologically active substance from the composition. The invention also discloses a process for making the composition which features addition of a non-hydrohalic acid effective to sustain and control the rate of release of an encapsulated biologically active substance from the vesicles at therapeutic levels in vivo.

US 2006/0078606 to Kim et al. provides a method for obtaining local anesthetics encapsulated in liposomes, such as multivesicular liposomes, with high encapsulation efficiency and slow release in vivo. When the encapsulated anesthetic is administered as a single intracutaneous dose, the duration of anesthesia and half-life of the drug at the local injection site is increased as compared to injection of unencapsulated anesthetic. The maximum tolerated dose of the encapsulated anesthetic is also markedly increased in the liposomal formulation over injection of unencapsulated anesthetic.

U.S. Pat. No. 7,547,452 to Atkins et al. provides sustained-release microparticle compositions. The microparticle composition can be formulated to provide extended release over a period of from about 7 days to about 200 days. The microparticles may be formulated with a biodegradable and biocompatible polymer, and an active agent, such as risperidone, 9-hydroxy-risperidone, and pharmaceutically acceptable acidic salts of the foregoing.

One local anesthetic formulation that has been used for short term post-surgical pain management is Naropin® Injection (ropivacaine hydrochloride monohydrate). Naropin® Injection is a sterile, isotonic solution that contains the enantiomer of bupivacaine, sodium chloride for isotonicity and water for injection. Sodium hydroxide and/or hydrochloric acid may be added for pH adjustment. Naropin® Injection is administered parenterally.

Naropin® Injection, however, has a relatively short duration of effect (4-6 hours). As a result, multiple repeated doses are typically required, forcing the patient to remain hospitalized during treatment or using a mechanical pump pre calibrated and patient operated to infiltrate the surgical wound with the analgesic drug as pain returns. Naropin® Injection has a maximum allowed dosage since it may affect the CNS and is contraindicated to be used IV. As Naropin® Injection is often combined with per os taken opiates when administered to treat post-operative pain; it retains some of the disadvantages associated with opiate-based analgesic therapy.

U.S. Pat. No. 5,863,549 to Tarantino is directed to a method for making in vivo a lecithin gel which provides for the sustained release of a biologically active compound contained in the gel. This invention is also directed to a method for the sustained treatment of a human or of other mammals with a therapeutic amount of a biologically active compound using the gel for the sustained release of the biologically active compound. The biologically active compounds disclosed and exemplified are peptides and polypeptides.

US 2005/0287180 to Chen provides compositions that comprise a phospholipid component (that contains one or more phospholipids) and a pharmaceutically acceptable fluid carrier, where the phospholipid component is in the range from about 10% to about 90% of the total weight. The compositions may further comprise non-phospholipid filler materials, where the amount of the non-phospholipid filler materials is in the range from about 5% to about 50% of the total weight. In certain embodiments, the compositions may be injectable, non-liposomal, and/or in form of a gel or a paste. The compositions of the invention may be useful for repairing and augmenting soft and/or hard tissues or for sustained local drug delivery. One drug formulation exemplified is bupivicaine in a phospholipid paste with propylene glycol.

US 2012/0046220 to Chen et al. provides a clear depot comprising at least one hydrophilic water-soluble pharmaceutically active antibacterial agent selected from the group consisting of vancomycin, gentamicin, a pharmaceutically acceptable salt thereof and a mixture thereof, water, a phospholipid, an oil, optionally a pH adjusting agent, and a viscosity modifying agent selected from the group consisting of ethanol, isopropanol, and a mixture thereof, wherein the water present in the final depot formulation is no more than about 4 wt % relative to the total weight of the depot and the depot has a pH of between about 3 and about 6.

US 2012/0316108 to Chen et al. is directed to compositions and methods of preparation of phospholipid depots that are injectable through a fine needle.

Additional references describing phospholipid-based formulations include WO 89/00077, WO 02/32395, EP 0282405 and U.S. Pat. Nos. 4,252,793; 5,660,854; 5,693,337 and Wang et al., *Lyophilization Of Water-In-Oil Emulsions To Prepare Phospholipid-based Anhydrous Reverse Micelles For Oral Peptide Delivery,* 39 European Journal of Pharmaceutical Sciences, at 373-79 (2010).

There is a need for prolonged post-surgical analgesia achieved by a single application at the end of the surgical procedure. The known phospholipid based depot formulations suffer from the drawback of high viscosity making them difficult to administer, and lack of long term stability at ambient temperatures. There is an unmet need for stable depot formulations of local anesthetics with improved viscosity making them amenable to delivery to the required site of action.

SUMMARY OF THE INVENTION

The present invention provides a non-aqueous, pro-liposomal depot local anesthetic formulation, which advantageously create liposomes or other lipidic vesicular structures in situ upon contact with body fluids. The present invention further provides a process for manufacturing the depot formulations of the invention wherein the composition is not exposed to an aqueous phase at any stage of the manufacturing process. The composition is devoid of water except for residual moisture that may be present in the excipients used to make the composition.

Furthermore, the present invention provides a depot formulation essentially devoid of synthetic phospholipids, using only GRAS excipients. The compositions of the invention thus provide improved stability, increased therapeutic duration and decreased adverse effects of local anesthetic drugs.

The invention is based, in part, on the surprising discovery that an oily solution carrying a local anesthetic is retained in the tissue longer and provides improved sustained release properties relative to a gel or a gel-like formulation. According to some embodiments, the solution of the invention forms liposomes or micelles or other types of lipid assemblies in vivo, following the introduction of physiological body fluids into the surgical site, thereby releasing the local anesthetics over a sustained period of time. Accordingly, the pro-liposomal formulation is stable and can be stored at room temperature, which is advantageous with respect to transportation and storage of the formulations, as compared to liposomal formulations which require storage at 2-8° C. The formulation will retain its active ingredient and not burst upon contact with surfactants, thus will not release the anesthetic into the system as may be the case with liposomes when bursting.

In one aspect, the invention provides a non-aqueous pharmaceutical formulation comprising: a local anesthetic; a natural non-synthetic phospholipid or pharmaceutically acceptable salt thereof; a non-aqueous pharmaceutically acceptable carrier; and a co-solvent as a viscosity regulator.

In another embodiment the non-aqueous pharmaceutical formulation consists essentially of: a local anesthetic; a natural non-synthetic phospholipid or pharmaceutically acceptable salt thereof; a non-aqueous pharmaceutically acceptable carrier; and a co-solvent. In one embodiment the non-aqueous pharmaceutical formulation consists of: a local anesthetic; a natural non-synthetic phospholipid or pharmaceutically acceptable salt thereof; a non-aqueous pharmaceutically acceptable carrier; an anti-oxidant and a co-solvent as a viscosity regulator.

According to some embodiments, the composition is stable for at least 24 months at room temperature. According to some embodiments, the composition is stable for at least 12 months at room temperature. According to some embodiments, the composition is stable for at least 6 months at room temperature. According to some embodiments, the composition is stable for at least 1 month at room temperature.

According to some embodiments, the composition is stable for at least 24 months at room temperature. According to some embodiments, the composition is stable for at least 12 months at room temperature. According to some embodiments, the composition is stable for at least 6 months at room temperature. According to some embodiments, the composition is stable for at least 1 month at room temperature.

According to some embodiments the co-solvent is a non-aromatic co-solvent. According to some embodiments the non-aromatic co-solvent is an alcohol. In some embodiments, the alcohol is ethanol. In some embodiments, ethanol is present in the amount of about 1% to about 15% by weight. In some embodiments, ethanol is present in the amount of about 2% to about 10% by weight. In some embodiments, ethanol is present in the amount of about 4% to about 6% by weight.

In some embodiments the co-solvent serves as a viscosity regulator which renders the composition suitable for injection. In some embodiments the viscosity of the formulation is below 2500 cP. In some embodiments the viscosity of the formulation is below 2000 cP. In some embodiments the viscosity of the formulation is in the range of 1000-2500 cP. In some embodiments, the viscosity of the formulation is in the range of 1000-2000 cP.

In some embodiments, the composition is devoid of particles above 100 nm in size. In some embodiments, the composition is devoid of particles above 50 nm in size. In some embodiments, the composition is devoid of particles above 20 nm in size. In some embodiments the composition is devoid of particles above 10 nm in size. In some embodiments the composition is an essentially particle-free oily solution. In some embodiments the composition is a clear solution.

In some embodiments, a local anesthetic is present in the amount equivalent to about 0.2% to about 18% by weight. In some embodiments, a local anesthetic is present in the amount equivalent to about 1% to about 12% by weight. In other embodiments, a local anesthetic is present in the amount equivalent to about 2% to about 4% by weight. In some embodiments, a local anesthetic is present in the amount equivalent to about 3% to about 6% by weight. In some embodiments, the local anesthetic is ropivacaine. In some embodiments, ropivacaine is ropivacaine hydrochloride.

The local anesthetic, in some embodiments, has an experimental Log P hydrophobicity value of at least 1.5.

In some embodiments, the phospholipid is a naturally occurring phospholipid. In some embodiments, the phospholipid is present in the amount of about 10% to about 80% by weight. In some embodiments, the phospholipid is present in the amount of about 40% to about 60% by weight. In some embodiments, the phospholipid is present in the amount of about 45% to about 55% by weight. In some embodiments, the phospholipid does not include any synthetic phospholipid. In some embodiments the phospholipid does not include 1,2-dimyristoyl-sn-glycero-3-phosphoglycerol (DMPG) or a pharmaceutically acceptable salt thereof. In some embodiments, the natural non-synthetic phospholipid is phosphatidylcholine (PC) or a pharmaceutically acceptable salt thereof.

In some embodiments the formulation is essentially devoid of fillers, especially water insoluble or particulate fillers. In some embodiments the formulations are devoid of inert particulate or suspended materials such as microspheres.

In some embodiments, the formulation is essentially devoid of water. In another embodiment, essentially devoid of water as used herein refers to less than 0.5% v/v or w/w of the formulation. In other embodiments, essentially devoid of water as used herein refers to less than 0.2% v/v or w/w of the formulation. In specific embodiments the composition is devoid of water except for residual moisture that may be present in the excipients used to make the composition. In specific embodiments the residual moisture is below 0.3%. In specific embodiments the residual moisture is below 0.15%.

In some embodiments, the non-aqueous pharmaceutically acceptable carrier comprises sesame oil, cottonseed oil, safflower oil, or one or more triglycerides. Each possibility is a separate embodiment of the invention. In some embodiments, the non-aqueous pharmaceutically acceptable carrier is castor oil. In some embodiments, the non-aqueous pharmaceutically acceptable carrier is present in the amount of about 20% to about 50% by weight. In specific embodiments, the ratio of the natural non-synthetic phospholipid and the non-aqueous pharmaceutically acceptable carrier is in the range of 2.2:1 to 1.2:1. In another embodiment, the ratio of the natural non-synthetic phospholipid and the non-aqueous pharmaceutically acceptable carrier is in the range of 2:1 to 1:1.

In some embodiments, the pharmaceutical formulation further comprises an anti-oxidant. In some embodiments, the anti-oxidant is cysteine or a pharmaceutically acceptable salt thereof.

In another aspect, the invention provides a pro-liposomal, non-aqueous, oleaginous pharmaceutical formulation comprising: an anesthetic in an amount equivalent to about 0.2% to about 10% by weight; about 40% to about 60% by weight of phosphatidylcholine (PC); about 35% to about 55% by weight of castor oil; and about 2% to about 10% by weight of ethanol.

In another aspect, the invention provides a pro-liposomal, non-aqueous, oleaginous pharmaceutical formulation comprising: Ropivacaine in an amount equivalent to about 0.5% to about 5% by weight; about 40% to about 60% by weight of phosphatidylcholine (PC); about 35% to about 55% by weight of castor oil; and about 2% to about 10% by weight of ethanol.

In another aspect, the invention provides a method for treating pain comprising administering to a patient in need thereof the pharmaceutical formulation of any one of the above embodiments.

In some embodiments, the pharmaceutical formulation is administered as a depot formulation. In some embodiments, the pharmaceutical formulation is administered as a single dose. In some embodiments, the pharmaceutical formulation is administered by infiltration into an incision. In some embodiments, the pharmaceutical formulation is administered by injection into an incision. In some embodiments, the pharmaceutical formulation is administered by injection into an incision following the suturing of said incision.

In some embodiments, the pain is post-operative pain.

In some embodiments, the pharmaceutical formulation provides pain relief for at least about 24 hours. In some embodiments, the pharmaceutical formulation provides pain relief between 24 and 48 hours. In some embodiments, the pharmaceutical formulation provides pain relief for at least about 48 hours. In some embodiments, the pharmaceutical formulation provides pain relief between 48 and 72 hours. In some embodiments, the pharmaceutical formulation provides pain relief for at least about 72 hours.

In another aspect, the invention provides a method for making a pro-liposomal non-aqueous oleaginous pharmaceutical formulation, the method comprising: (a) mixing a non-aqueous pharmaceutically acceptable carrier with: (i) a local anesthetic; (ii) a natural non-synthetic phospholipid or pharmaceutically acceptable salt thereof; and (iii) a co-solvent, to provide a non-aqueous solution; (b) removing all or a portion of the co-solvent from the non-aqueous solution; (c) adding the same or a different co-solvent to the non-aqueous solution to a total amount of about 2% to about 12% by weight.

According to some embodiments, the pharmaceutical formulation prepared by the method is a clear solution, devoid of particles above 100 nm in size, stable at ambient temperature and substantially devoid of water.

According to some embodiments, the pharmaceutical formulation prepared by the method is a clear solution, devoid of particles above 50 nm in size, stable at ambient temperature and substantially devoid of water.

In some embodiments, removing all or a portion of the co-solvent from the non-aqueous solution results in an oleaginous solution.

According to the present invention the process does not include exposure to an aqueous phase and does not involve emulsification steps.

In some embodiments, the non-aqueous pharmaceutically acceptable carrier comprises castor oil. In some embodiments, the method further comprises mixing the non-aqueous pharmaceutically acceptable carrier with an anti-oxidant.

In some embodiments, the co-solvent is removed from the non-aqueous solution by evaporation and/or vacuum drying. In alternative embodiments the process does not use excess co-solvent as a viscosity regulator and therefore there will be no need for evaporation or vacuum drying.

In some embodiments, the method further comprises autoclaving the resultant formulation.

In another aspect, the invention provides a kit comprising: a container containing the pharmaceutical formulation of any of the above embodiments; and instructions for use.

In another aspect, the invention provides a pre-filled syringe comprising the pharmaceutical formulation of any one of the above embodiments.

There is provided herein, according to another aspect of the invention, a pro-liposomal, non-aqueous stock formulation comprising all of the excipients of the depot formulation without the local anesthetic, and a process for manufacturing same. In specific embodiments, the pro-liposomal, non-aqueous stock formulation comprises: a natural non-synthetic phospholipid; a non-aqueous pharmaceutically acceptable carrier; and a co-solvent as a viscosity regulator. According to another embodiment, the stock formulation is highly stable and may be stored for prolonged periods of time before the addition of a local anesthetic.

According to some embodiments, the composition is stable for at least 24 months at room temperature. According to some embodiments, the composition is stable for at least 12 months at room temperature. According to some embodiments, the composition is stable for at least 6 months at room temperature. According to some embodiments, the composition is stable for at least 1 month at room temperature.

In specific embodiments, the stock formulation is substantially devoid of water. In specific embodiments the stock formulation is devoid of water except for residual moisture that may be present in the excipients used to make the depot. In specific embodiments the residual moisture is below 0.3%. In specific embodiments the residual moisture is below 0.15%.

In specific embodiments, the viscosity of the stock formulation is in the range of 1000-2500 cP. In some embodiments, the viscosity of the stock formulation is in the range of 1000-2000 cP.

In some embodiments, the stock formulation is devoid of particles above 100 nm in size. In some embodiments, the stock formulation is devoid of particles above 50 nm in size. In some embodiments, the stock formulation is devoid of particles above 20 nm in size. In some embodiments the stock formulation is devoid of particles above 10 nm in size. In some embodiments the stock formulation is an essentially particle-free oily solution. In some embodiments the composition is a clear solution.

In another aspect, the invention provides a method for making a pro-liposomal, non-aqueous, stock formulation comprising all of the excipients of the depot formulation without the local anesthetic. The method comprising: (a) equilibrating a non-aqueous pharmaceutically acceptable carrier; and (b) dissolving a natural non-synthetic phospholipid in said non-aqueous pharmaceutically acceptable carrier by heating and mixing. According to some embodiments the method further comprises adding a co-solvent at step (a). Alternatively, the method comprises adding a co-solvent at step (b) of the method. It is to be understood that the method can be a continuous process in which all ingredients are added and processed simultaneously.

According to some embodiments, the stock formulation prepared by the method is a clear solution, devoid of particles above 100 nm in size, stable at ambient temperature and substantially devoid of water. According to some embodiments, the stock formulation prepared by the method is a clear solution, devoid of particles above 50 nm in size, stable at ambient temperature and substantially devoid of water.

It was surprisingly found that a combination of heat, torque and high shear mixing resulted in the in complete dissolving of the phospholipid in the pharmaceutically acceptable non-aqueous carrier. Accordingly, there is advantageously no need for adding excess ethanol and subsequent evaporation of the ethanol.

In specific embodiments, an anti-oxidant is added to the co-solvent prior to mixing the co-solvent into the stock formulation. Alternatively, the anti-oxidant is added separately at any of steps (a) or (b) of the method or separately simultaneously with the addition of all other ingredients.

In specific embodiments, equilibrating the non-aqueous pharmaceutically acceptable carrier (and optionally the co-solvent and anti-oxidant) comprises heating to at least about 50° C. In another embodiment, equilibrating the non-aqueous pharmaceutically acceptable carrier (and optionally the co-solvent and anti-oxidant) comprises heating to at least about 65° C. In another embodiment, equilibrating the non-aqueous pharmaceutically acceptable carrier comprises heating to at least about 85° C.

In specific embodiments no stages of the method comprise exposure to an aqueous phase or emulsification.

In specific embodiments, no stages of the manufacturing process comprise excess ethanol. Hence using this method, there is advantageously no need evaporation of ethanol in presence of the local anesthetic thereby favorably avoiding any excessive waste of the local anesthetic.

The invention is based, in part, on the surprising discovery that the stock formulation is a ready-to-use stock formulation into which a local anesthetic is easily mixed without further processing of the formulation. As such, any local anesthetic described in the above embodiments can be added to the stock formulation forming a pro-liposomal, non-aqueous, pharmaceutical composition. Alternatively, the local anesthetic is dissolved prior to being added to the stock formulation.

In specific another embodiments, the method further comprises autoclaving the resultant stock formulation.

There is provided herein, according to another aspect of the invention, a method for making a pro-liposomal non-aqueous pharmaceutical composition comprising: (a) equilibrating a non-aqueous pharmaceutically acceptable carrier; and (b) dissolving a natural non-synthetic phospholipid in said non-aqueous pharmaceutically acceptable carrier by heating and mixing. The method further comprises adding a co-solvent at step (a) or (b). According to some embodiments, a local anesthetic is added at step (a) of the method. According to some embodiments, a local anesthetic is added at step (b) of the method. According to some embodiments, a local anesthetic is added at an additional step (c) of the method.

According to some embodiments, the pharmaceutical composition is prepared by the method is a clear solution, devoid of particles above 100 nm in size, stable at ambient temperature and substantially devoid of water. According to some embodiments, the pharmaceutical composition is prepared by the method is a clear solution, devoid of particles above 50 nm in size, stable at ambient temperature and substantially devoid of water. According to some embodiments, the method enables adding the local anesthetic to the pre-prepared stock formulation without further processing. Alternatively, the method is continuous meaning that all or at least a part of the ingredients are added and processed simultaneously.

According to another aspect of the invention, there is provided a kit comprising a container containing the stock formulation of any of the above embodiments. In specific embodiments, the kit further comprises a local anesthetic.

According to another aspect of the invention, there is provided a pro-liposomal non aqueous stock formulation prepared by the method of any of any of the above embodiments.

In another embodiment, the invention provides a method of treating or relieving pain comprising administering to a subject in need thereof an effective amount of the pharmaceutical composition of any of the above embodiments. In another aspect, the invention provides a pharmaceutical composition of any of the above embodiments for use in treating or relieving pain. In some embodiments, the pharmaceutical composition comprises ropivacaine.

BRIEF DESCRIPTION OF THE DRAWINGS

The invention is described with reference to the following figures, which are presented for purposes of illustration only and which are not intending to be limiting to the invention.

FIG. 1A shows the results obtained for depot formulation A/saline (1:1), FIG. 1B shows the results obtained for depot formulation A/pig plasma (1:1).

DETAILED DESCRIPTION OF THE INVENTION

Figure 1A:
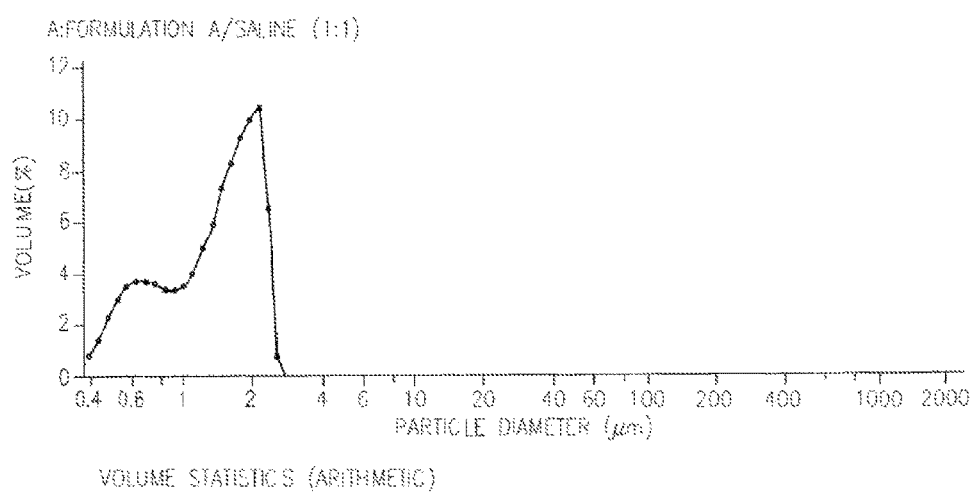
FIGS. 1A and 1B show the results of a particle size distribution test obtained using a coulter LS230 particle size analyzer.
Figure 1B:
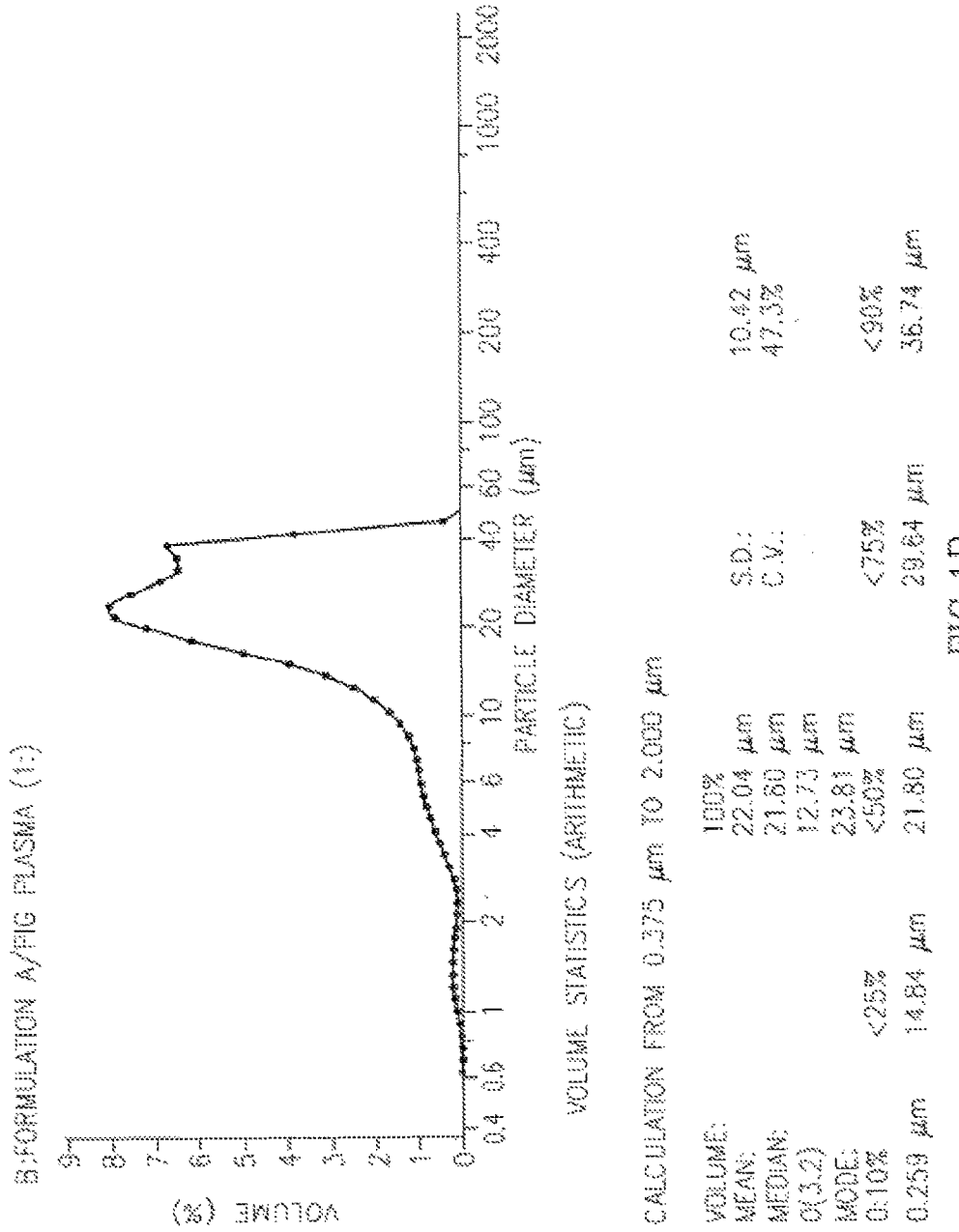

The present invention provides a non-aqueous, pro-liposomal depot formulation for a local anesthetic and a process for manufacturing same in which no steps of emulsification are involved, and the composition is not exposed to an aqueous phase at any stage. Furthermore, the present invention provides a depot formulation essentially devoid of synthetic phospholipids, using only GRAS excipients.

The present invention also provides a pro-liposomal, non-aqueous stock formulation comprising all of the excipients of the depot formulation without a local anesthetic, and a process for manufacturing same. The stock formulation is ready for the addition of the local anesthetic and is substantially devoid of water.

Definitions and Abbreviations

As used herein, "local anesthetic" refers to any known local anesthetic including pharmaceutically salts, solvates, racemates, and isomers thereof. As used herein, "ropivacaine" refers to ropivacaine, a pharmaceutically acceptable salt of ropivacaine, a solvate of ropivacaine, or a solvate of a pharmaceutically acceptable salt of ropivacaine. For example, the term "ropivacaine," as used herein, includes ropivacaine hydrochloride monohydrate. When amounts or percentages of ropivacaine are discussed herein, a percentage of about 4.78% of ropivacaine HCl monohydrate by weight is considered equivalent to a percentage of about 4% of ropivacaine base by weight. Similarly, a percentage of about 0.63%, 1.19% or 2.39% of ropivacaine HCl monohydrate by weight is considered equivalent to a percentage of about 0.5-2% of ropivacaine base by weight.

As used herein, "solvate" refers to a molecular complex comprising a compound or a salt of the compound and one or more pharmaceutically acceptable solvent molecules, for example, one or more ethanol molecules.

As used herein, "hydrate" refers to a solvate in which the one or more solvent molecules are water molecules.

As used herein, "non-aqueous formulation" refers to a formulation in which the solvent does not comprise water. A "non-aqueous formulation" is essentially devoid of water or comprises less than 0.5%, 0.4%, 0.3%, or 0.2% w/w or v/v water. A "non-aqueous formulation," however, can contain trace amounts of water (up to 0.5% w/w), such as water present in one of the solutes, e.g., water present in ropivacaine hydrochloride monohydrate.

As used herein "non-aqueous formulation" refers to a formulation devoid of emulsion in any of its preparation stages. Dissolving the anesthetic may be obtained by sonication in a water bath sonicator heated to about 50° C.

As used herein, "pro-liposomal formulation" refers to a formulation that is free of detectable amount of liposomes before use or under storage conditions. In another embodiment, liposomes are formed upon contact with living tissue fluids. In another embodiment, liposomes are formed in-vivo. In another embodiment, the non-liposomal formulation is a pro-liposomal formulation (liposomes are formed in-vivo upon contact with body fluids).

As used herein, "viscosity" refers to the resistance of the composition to gradual deformation by shear stress or tensile stress. According to some embodiments the composition has a viscosity in the range of 1000-3000 cP, 1250-2500 cP, 1400-2000 cP, 1500-1850 cP. Each possibility is a separate embodiment of the invention.

As used herein "injectable" refers to a formulation that can be injected or infiltrated into a wound using a needle ranging from 18-30 Gauge, 20-25 Gauge, 21-23 Gauge needle. Each possibility is a separate embodiment of the invention.

As used herein, "about" means within ±10% of the value that follows it. For example, "about 100" means between 90 and 110, including 90 and 110; "about 5%" means between 4.5% and 5.5%, including 4.5% and 5.5%.

As used herein, "phospholipid" refers to a molecule that comprises at least one phosphate head group and at least one non-polar tail group. As used herein, "phospholipid" is limited to natural non-synthetic phospholipid. As used herein, "phospholipid" is limited to a naturally occurring phospholipid.

As used herein, "oleaginous solution" refers to a solution with oil-like viscosity. An oleaginous solution has lower viscosity than a gel, a paste, a paste-like or a gel-like formulation. As used herein, "oleaginous liquid" refers to a liquid with oil-like viscosity. An oleaginous liquid has lower viscosity than a gel, a paste, a paste-like or a gel-like liquid.

As used herein, "co-solvent" refers to a substance that increases the solubility of the therapeutic agent within the formulation and/or reduces the formulation viscosity thereby rendering the formulation suitable for injection. According to some embodiments the co-solvent is a non-aromatic co-solvent.

As used herein the term "stable composition" refers to compositions which do not form precipitates when stored at ambient temperature.

As used herein the term "ambient temperature" and "room temperature" interchangeably refer to a temperature in the range of 20-25° C.

As used herein the term "clear solution" refers to essentially transparent solutions devoid of particles above 100 nm. Alternatively, the term "clear solution" refers to essentially transparent solutions devoid of particles above 50 nm. Alternatively, the term "clear solution" refers to essentially transparent solutions devoid of particles above 20 nm.

As used herein the term "devoid of particles above 100 nm" refers to solutions containing less than 5% particles above 100 nm. As used herein the term "devoid of particles above 50 nm" refers to solutions containing less than 5% particles above 50 nm. As used herein the term "devoid of particles above 20 nm" refers to solutions containing less than 5% particles above 20 nm.

As used herein the terms "filler" and "non-phospholipid filler component" interchangeably refer to a biodegradable or non-biodegradable material such as but not-limited to poly lactide-co-glycolide (PLGA), hydroxyapatite, microspheres of polymethylmethacrylate (PMMA), which may be adapted for use as tissue fillers.

As used herein, unless specifically indicated otherwise, "by weight" refers to w/w. As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

As used herein, unless specifically indicated otherwise, the word "or" is used in the inclusive sense of "and/or" and not the exclusive sense of "either/or". In one embodiment, the term "comprising" includes "consisting".

As used herein, the singular forms "a", "an", and "the" also include plural referents unless the context clearly indicates otherwise.

As used herein, "subject" refers to any animal, including but not limited to humans, non-human primates and other mammals, reptiles and birds.

The following abbreviations are used herein and have the indicated definitions: SC is subcutaneous, IM is intramuscular, IV is intravenous, PC is phosphatidylcholine, PCA is patient controlled analgesia, NSAID is non-steroidal anti-inflammatory analgesic, DMPG is 1,2-dimyristoyl-sn-glycero-3-phosphoglycerol or a salt or a salt combination thereof, NAC is N-acetyl-L-cysteine, CTMC is 2-carboxy-2,5,7,8-tetrumethyl-G-chromanol, GP is Guinea pig, DS is domestic swine, NBF is neutral buffered formulation, RT is room temperature.

Extended Release Depot Formulations

Administration of a depot formulation is useful for the gradual release of an active therapeutic agent. In further embodiments, administration of a depot formulation that forms liposome-like structures in-vivo is useful for the gradual release of an active therapeutic agent. In some embodiments, an active therapeutic agent is formulated with carriers that provide a gradual release of the active therapeutic agent over a period lasting from few hours to a number of days. Depot formulations are often based upon a degrading matrix which gradually disperses in the body to release the active therapeutic agent. Depot formulations can be designed to either allow or prevent an initial burst release of the active agent. All components of depot formulations are biocompatible and biodegradable. In some embodiments, the terms "composition" and "formulation" are used interchangeably. In some embodiments, the terms: "depot formulation", "depot composition", "formulation of the invention", "pro-liposomal formulation", "oleaginous formulation", and "non-aqueous formulation" are used interchangeably.

In this context it is to be understood that the formulations of the invention are pro-liposomal, non-aqueous, RT stable uniform solutions from completion of production throughout storage and up to and including the time of application. In situ, after penetration into a subject, upon contact with the bodily fluids they spontaneously form liposomes or other vesicles or micelles.

Furthermore, the extended release depot formulations described herein minimize the burdens of patient compliance as they require a less frequent pain killer dosing regimen, thereby reducing the untoward side effects of such pain killers, the frequency of clinic visits, the amount of clinical support needed as well as the overall time and hospitalization costs of treatment. In addition, depending on the active therapeutic agent it contains, the depot formulation described herein can reduce the risks of drug abuse (such as abuse of opioid drugs) by eliminating or reducing the need for take-home medication.

In some embodiments, the depot formulations described herein are non-liposomal. In another embodiment, the depot formulations described herein are non-liposomal and non-aqueous. In other embodiments, the depot formulations described herein are oleaginous but non-liposomal and non-aqueous. In some embodiments, the depot formulation forms liposomes upon in-vivo entry to a target tissue. In another embodiment, the depot formulation forms liposomes upon contact with a living tissue or bodily fluids.

Extended Release Depot Formulations for Treatment of Pain, Including Post-Operative Pain Local Anesthetics Local anesthetics are useful active therapeutic agents for treatment of post-surgical pain. They can be formulated as extended release depot formulations described herein. Local anesthetics include, but are not limited to: articaine, bupivacaine, carticaine, cinchocaine/dibucaine, etidocaine, levobupivacaine, lidocaine/lignocaine, mepivacaine, piperocaine, prilocaine, ropivacaine, trimecaine, procaine/benzocaine, chloroprocaine, cocaine, cyclomethycaine, dimethocaine/larocaine, propoxycaine, procaine/novocaine, proparacaine, tetracaine/amethocaine, lidocaine/prilocaine, saxitoxin, tetrodotoxin and pharmaceutically acceptable salts thereof. Each possibility is a separate embodiment of the invention. Of course, a combination of two or more of these local anesthetics can also be used in the depot formulations described herein.

Phospholipids

Phospholipids are useful components of the extended release depot formulations described herein. A phospholipid comprises at least one polar head group and at least one non-polar tail group, wherein at least one of the polar head groups is a phosphate group. The non-polar portions can be derived from the fatty acids. A phospholipid will typically contain two non-polar groups, although a single non-polar group is sufficient. Where more than one non-polar group is present these may be the same or different. Suitable phospholipid polar head groups include, but are not limited to, phosphatidylcholine (PC), phosphatidylethanolamine, phosphatidylserine, and phosphatidylinositol.

It was surprisingly found that the enhanced properties associated with the present formulation are linked to a naturally occurring phospholipid and not to a synthetic phospholipid such as but not limited to DMPG. Therefore, the phospholipid, in some embodiments, is a naturally-occurring phospholipid. Suitable sources of phospholipids include egg, heart (e.g., bovine), brain, liver (e.g., bovine) and plant sources including soybeans. Naturally occurring phospholipids tend to cause lesser amounts of inflammation and reaction from the body of the subject. Not only is this more comfortable for the subject, but it may increase the residence time of the resulting depot formulation, especially for parenteral depot formulations, since less immune system activity is recruited to the administration site.

Phospholipids include lipid molecules derived from either glycerol (phosphoglycerides, glycerophospholipids) or sphingosine (sphingolipids). They include polar lipids, and certain phospholipids that are important in the structure and function of cell membranes, and are the most abundant of membrane lipids.

Some phospholipids are triglyceride derivatives in which one fatty acid has been replaced by a phosphorylated group and one of several nitrogen-containing molecules. The fatty acid chains are hydrophobic. However, the charges on the phosphorylated and amino groups make that portion of the molecule hydrophilic. The result is an amphiphilic molecule.

Amphiphilic phospholipids are major constituents of cell membranes. These molecules form a phospholipid bilayer with their hydrophilic (polar) heads facing their aqueous surroundings (e.g., the cytosol) and their hydrophobic tails facing each other. The most naturally abundant phospholipid is phosphatidylcholine (PC).

Phospholipids are available from naturally occurring sources or can be made by organic synthesis. Lecithin is a naturally occurring mixture of the diglycerides of stearic, palmitic, and oleic acids, linked to the choline ester of phosphoric acid, commonly called phosphatidylcholine. Hydrogenated lecithin is the product of controlled hydrogenation of lecithin.

Lecithin-Based Naturally-Occurring Phospholipids

According to the United State Pharmacopoeia (USP), lecithin is a non-proprietary name describing a complex mixture of acetone-insoluble phospholipids, which consists mainly of phosphatidylcholine (PC), phosphatidylethanolamine (PE), phosphatidylserine (Ptd-L-Ser or PS), and phosphatidylinositol (PtdIns, or PI), combined with various amounts of other substances such as triglycerides, fatty acids, and carbohydrates. The composition of lecithin and hence its physical properties vary depending upon the source of the lecithin and the exact phospholipid composition, e.g., phosphatidylcholine content, etc. Commercially available lecithin products (lecithins) have two primary sources: egg yolk and soybeans. Lecithins include: lecithin (general), soybean lecithin or soy lecithin, and egg yolk lecithin or egg lecithin.

Lecithin is a component of cell membranes and is therefore consumed as a normal part of human diet. It is highly biocompatible and virtually nontoxic in acute oral studies, short-term oral studies, and sub-chronic dermal studies in animals. Lecithin and hydrogenated lecithin are generally nonirritating and nonsensitizing in animal and human skin cosmetics (See, Fiume Z, 2001 "Final report on the safety assessment of Lecithin and Hydrogenated Lecithin", *Int J Toxicol.*; 20 Suppl 1:21-45).

Pharmaceutically, lecithins are mainly used as dispersing, emulsifying, and stabilizing agents and are included in intramuscular (IM) and intravenous (IV) injections, parenteral nutritional formulations and topical products. Lecithin is also listed in the FDA Inactive Ingredients Guide for use in inhalations, IM and IV injections, oral capsules, suspensions and tablets, rectal, topical, and vaginal preparations. Cosmetically, lecithin and hydrogenated lecithin are safe as used in rinse-off cosmetic products; they may be safely used in leave-on products at concentrations up to 15%, the highest concentration tested in clinical irritation and sensitization studies cosmetics.

One source of lecithin-based phospholipids suitable for the depot formulations described herein is soy lecithin of high purity, i.e., free from allergenic, inflammatory agents or agents that cause other deleterious biological reactions, which is qualified for use in injectable products. Such injectable forms of soy lecithin are commercially available in the brand names of Phospholipon® by Phospholipid GmbH (Cologne, Germany), Lipoid® S by Lipoid GmbH (Ludwigshafen, Germany), Epikuron® by Evonik Industries (Parsippany, N.J.—formerly Degussa). These refined soy lecithin products may contain different concentrations of phosphatidylcholine (PC) content ranging from 30% to 100%. By combining lecithin products of different PC contents, it is possible to vary the consistency of the implant and persistence in the tissue. A specific example of soy lecithins is Phospholipon® 90G, which is pure phosphatidylcholine stabilized with 0.1% ascorbyl palmitate.

Other Naturally-Occurring Phospholipids

Other examples of phospholipids from naturally-occurring sources that may be used on the depot formulations described herein include, but are not limited to, sphingolipids in the form of sphingosine and derivatives (from soybean, egg, brain or milk), phytosphingosine and derivatives (from yeast), phosphatidylethanolamine, phosphatidylserine, and phosphatidylinositol.

Total Phospholipid Content in the Depot Formulations

Optionally, the depot formulations described herein comprise more than one phospholipid. The combined amount (w/w) of all phospholipids in the depot formulation is referred to as total phospholipid content.

The total phospholipid content of the depot formulations described herein is generally in the range of about 10% to about 80% of the total weight of the depot formulation. In some embodiments, the minimum total phospholipid content (w/w) of in the depot formulation is about 10%, 15%, 20%, 25%, 30%, 35%, 40%, 45%, 50%, 60%, 70%, 75%, or 80% (including any value between 10% and 80%). In some embodiments, the maximum total phospholipid content (w/w) in the depot formulation is about 40%, 45%, 50%, 55, 60%, or 70% (including any value between 40% to 60%). In some embodiments, the total phospholipid content is between the value minimum phospholipid contents and the value of the maximum phospholipid content.

Non-Aqueous Pharmaceutically Acceptable Carriers

In one embodiment, the non-aqueous pharmaceutically acceptable carrier comprises sesame oil, cottonseed oil, safflower oil, or one or more triglycerides. In another embodiment, the non-aqueous pharmaceutically acceptable carrier is castor oil. In some embodiments, the non-aqueous pharmaceutically acceptable carrier is a surface-active agent. In some embodiments, the non-aqueous pharmaceutically acceptable carrier is present in the amount of about 20% to about 60% by weight. In yet another embodiment, the non-aqueous pharmaceutically acceptable carrier is present in the amount of about 30% to about 50% by weight.

In yet another embodiment, the ratio between the phospholipids and the non-aqueous carrier is in a range of 3:1-1:2, 2.5:1-1:5:, 2.2:1-1:1.2, 2:1-1:1. Each possibility is a separate embodiment of the invention.

Co-solvent

In some embodiments, the formulation further comprises a co-solvent. According to some embodiments the co-solvent is a non-aromatic co-solvent. In some embodiments the co-solvent might be, but is not limited to: ethanol, propylene glycol, glycerol, dimethylacetamide, dimethyl isosorbide, dimethyl sulfoxide, N-methyl-2-pyrrolidinone, and the like. In some embodiments, the co-solvent is glycerol. In some embodiments, the co-solvent is ethanol. In some embodiments, the co-solvent is alcohol USP which contains between 94.9 and 96.0% v/v ethyl alcohol. In another embodiment, the co-solvent is present in the formulation in an amount of 1-15% by weight. In another embodiment, the co-solvent is present in the formulation in an amount of 0.5-10% by weight. In another embodiment, the co-solvent is present in the formulation in an amount of 4-8% by weight. In another embodiment, the co-solvent is present in the formulation in an amount of 5-7% by weight. In another embodiment, the co-solvent is present in the formulation in an amount of 5.5-6.5% by weight. It was surprisingly found that when using aromatic co-solvents, such as but not limited to benzyl alcohol, administration of the composition into to incision wound of a guinea pigs caused adverse reactions such as irritations of the skin at the site of application.

Viscosity Modifying Agents

In some embodiments the co-solvent serves as a viscosity regulator which renders the composition suitable for injection through 18-25 G injection needles. In another embodiment, the co-solvent serves as a viscosity regulator which renders the composition suitable for injection through a 21 G needle.

According to some embodiments, adding ethanol to the depot formulation does not negatively affect either the activity, nor the blood and wound concentration or the stability of local anesthetics of low water solubility such as ripovavaine, but enhances the flowability by reducing viscosity, thus enhancing injectability of the formulation and allows the use of much smaller diameter injection needles.

Moreover, as illustrated by the liposome formation assays, addition of the viscosity modifying agent ethanol to the depot formulation does not negatively influence the ability to form liposomes upon exposure to aqueous surroundings and subsequently to ensure the slow release of the local anesthetic.

In some embodiments the viscosity of the formulation is below 2500 cP. In some embodiments the viscosity of the formulation is below 2000 cP. In another embodiment, the viscosity of the formulation is preferably in the range of 1000-3000 cP, 1000-2500 cP, 1000-2000 cP, 1250-2000 cP, 1500-2000 cP, 1500-1850 cP. Each possibility is a separate embodiment of the invention.

It was surprisingly found that in order to increase residence time and duration of activity, the composition should have a viscosity in the range of 1000-2000 cP despite the decreased injectability as a result thereof. For example, as shown in Example 5 below, a formulation according to the present invention showed maintenance of higher ropivacaine concentrations in the vicinity of the wound even four days after injection.

Anti-Oxidants

In some embodiments, the extended release depot formulations comprise one or more anti-oxidants. Anti-oxidants can be used to prevent or reduce oxidation of the phospholipids in the depot formulations described herein. Any non-toxic biocompatible anti-oxidant can be used for this purpose. Exemplary anti-oxidants include, but are not limited to, ascorbic acid (vitamin C), cysteine (L-cysteine), N-acetyl-L-cysteine (NAC), L-carnitine, acetyl-L-carnithine, alpha lipoic acid, glutathione, alpha tocopherol (vitamin E), 2-carboxy-2,5,7,8-tetramethyl-6-chromanol (CTMC), ascorbyl palmitate and uric acid. Pharmaceutically acceptable salts of these or other anti-oxidants are also considered "anti-oxidants" and can be used in the depot formulations described herein. These exemplary anti-oxidants mentioned above are commercially available from a variety of sources.

Excipients

Various excipients can be included in the depot formulations of local anesthetics.

Examples of suitable pharmaceutical excipients are described in *Remington's Pharmaceutical Sciences* 1447-1676 (Alfonso R. Gennaro eds., 19th ed. 1995) and in Strickley R., "Solubilizing Excipients in Oral and Injectable Formulations," *Pharmaceutical Research*, Vol. 21, No. 2, February 2004, pp. 201-230, both of which are incorporated herein by reference in their entirety.

Where necessary, the depot formulations of a local anesthetic can also include a solubilizing agent. Generally, the ingredients are supplied either separately or mixed together in unit dosage form, for example, as a dry lyophilized powder or water-free concentrate in a hermetically sealed container such as an ampule or sachette indicating the quantity of active agent.

Pro-Liposomal, Non-Aqueous Depot Formulations

In some embodiments, the extended release depot formulations are non-aqueous, oleaginous, or any combination thereof. The formulations can comprise (a) a local anesthetic; (b) a first phospholipid or a pharmaceutically acceptable salt thereof; (c) optionally, a second phospholipid or a pharmaceutically acceptable salt thereof; (d) a non-aqueous pharmaceutically acceptable carrier such as but not limited to an oil; and (e) a co-solvent such as but not limited to an alcohol. In some embodiments the depot is pro-liposomal and forms liposomes in situ.

In some embodiments, the composition is devoid of particles above 100 nm. In some embodiments, the composition is devoid of particles above 50 nm in size. In some embodiments, the composition is devoid of particles above 20 nm in size. In some embodiments, the composition is devoid of particles above 10 nm in size. In some embodiments the composition is an essentially particle-free oily solution. In some embodiments the composition is a clear solution.

Prior art formulations (see US 2012/0316108) prepared according to a method of preparation involving forming a nanodispersion which is subsequently lyophilized to obtain an anhydrous gel, fail to form clear solutions and contain particles. In other words these are nanodispersions rather than clear solutions.

The local anesthetic can be articaine, bupivacaine, carticaine, cinchocaine/dibucaine, etidocaine, levobupivacaine, lidocaine/lignocaine, mepivacaine, piperocaine, prilocaine, ropivacaine, trimecaine, procaine/benzocaine, chloroprocaine, cocaine, cyclomethycaine, dimethocaine/larocaine, propoxycaine, procaine/novocaine, proparacaine, tetracaine/amethocaine, lidocaine/prilocaine, saxitoxin, tetrodotoxin, a combination thereof, or a pharmaceutically acceptable salt thereof. According to some embodiments the local anesthetic is ropivacaine.

A combination of two or more of these active pharmaceutical ingredients (APIs) or their pharmaceutically acceptable salts can also be used. The concentration of the API is generally between 0.2% to about 10%, or about 2% to about 4%, or is equivalent to about 0.2% to about 10%, or about 2% to about 4% of the free base or free acid of the compound (e.g., if the local anesthetic is in a form of a salt and/or a hydrate). Obviously, the concentration of the local anesthetic will depend on the specific local anesthetic used and on the length or profile of the pain relief desired.

The amount of the local anesthetic in the depot formulation will, of course, depend on: which local anesthetic is used, the current maximal onetime amount allowed, the medical indication, the patient, etc. In some embodiments the amount of the anesthetic is about 0.2% to about 10% by weight and in some embodiments the amount is about 2% to about 4% by weight.

In some embodiments, the natural non-synthetic phospholipid can be any of the phospholipids described above. In some embodiments, the natural non-synthetic phospholipid is present in the formulation in the amount of about 10% to about 80% by weight. In some embodiments, the phospholipid is not a synthetic lipid such as 1,2-dimyristoyl-sn-glycero-3-phosphoglycerol (DMPG) or a pharmaceutically acceptable salt thereof. In another embodiment, the formulation of the invention is devoid of 1,2-dimyristoyl-sn-glycero-3-phosphoglycerol (DMPG) or a pharmaceutically acceptable salt thereof. In other embodiments, the compositions of the invention are substantially devoid of DMPG. In this context devoid of DMPG refers to a concentration below 0.5%, preferably below 0.1%.

In some embodiments, the non-synthetic phospholipid is present in the formulation in the amount of about 40% to about 60% by weight. In some embodiments, the phospholipid is phosphatidylcholine (PC) or a pharmaceutically acceptable salt thereof.

In some embodiments, the non-aqueous pharmaceutically acceptable carrier is present in the formulation in the amount of about 20% to about 50% by weight. In some embodiments, the non-aqueous pharmaceutically acceptable carrier is castor oil, sesame oil, cottonseed oil, safflower oil, or one or more triglycerides.

In some embodiments, the co-solvent is a non-aromatic co-solvent. In some embodiments, the co-solvent is an alcohol. In some embodiments, the alcohol is ethanol. Ethanol can be present in the formulations in the amount of about 1% to about 15% by weight. In some embodiments the co-solvent serves as a viscosity regulator which renders the composition suitable for injection. In some embodiments the viscosity of the formulation is below 2500 cP. In some embodiments the viscosity of the formulation is below 2000 cP. In some embodiments the viscosity of the formulation is in the range of 1000-2500 cP. In some embodiments, the viscosity of the formulation is in the range of 1000-2000 cP. The non-aqueous pro-liposomal depot formulations optionally comprise an anti-oxidant. Suitable anti-oxidants have been described above.

The non-aqueous non-liposomal depot formulations can optionally comprise additional ingredients, such as various excipients, pH modifying agents, metal chelators such as EDTA or edetic acid, salts, coloring agents and the like.

According to some embodiments the formulation is devoid of sugars such as but not limited to sucrose, dextrose, lactose, glucose, trehalose, maltose, mannitol, sorbitol, glycerol, amylose, starch, amylopectin, or a mixture thereof.

While the pro-liposomal non-aqueous depot formulation described herein are termed non-aqueous (or essentially devoid of water), residual or trace water molecules, e.g., from ingredients used to make the formulation, may remain present. Such depot formulation is still deemed to be non-aqueous. In some embodiments, water trigger the formation of liposomes and therefore the depot formulation must be devoid of water or at least have minute amount of water as described herein. In specific embodiments the residual moisture was below 0.3%. In specific embodiments the residual moisture was below 0.15% as determined using the Karl Fischer method. Thus, in some embodiments, liposomes are formed within the depot formulation upon contact with aqueous body fluids (such as contact with a living a tissue which comprises water). In some embodiments, the formulation of the present invention is prepared and stored in dry conditions which ensure that the compositions are essentially "waterless" and that the liposomes can form only after administration to the bodily fluids in situ.

Methods for Making Non-Liposomal Non-Aqueous Formulations

In some embodiments, pro-liposomal non-aqueous depot formulations of the invention are prepared as follows:

1. A local anesthetic (e.g., ropivacaine), a natural non-synthetic phospholipid (e.g., Phospholipon® 90G), a pharmaceutically acceptable non-aqueous carrier (e.g., castor oil), and optionally, an anti-oxidant (e.g., cysteine HCl) are dissolved in a co-solvent (such as an alcohol e.g., ethanol) by warming and/or sonication, and/or any other means for dispersing and/or mixing the ingredients.
2. The excess alcohol is removed or partially removed, e.g., by evaporation and/or vacuum pump drying. Other processes can also be used for the removal of the alcohol, or the formulation is produced with the exact amount of ethanol in the final formulation.
3. Optionally, the amount of residual alcohol in the end product of step 2 is pre-determined.
4. If required, additional amounts of the same or a different co-solvent may be added and mixed with the product of step 2 to a final alcohol concentration of about 4-8% (w/w). The final alcohol concentration of 6% (w/w) has been determined to work well.
5. Optionally, the product of step 4 is transferred to vials and/or sterilized (e.g., by autoclaving).

Various modifications to this procedure are also contemplated. However, water is not added as a processing aid or as an excipient in the manufacturing process of the pro-liposomal non-aqueous depot formulations. As no water is added during the preparation process no lyophilization step is required. In effect, the preparation of the composition does not require the addition of sugars, such as but not limited to sucrose, dextrose, lactose, glucose, trehalose, maltose, mannitol, sorbitol, glycerol, amylose, starch, amylopectin, or a mixture thereof. The addition of sugars is often required to avoid aggregation of phospholipid particles or droplets during the water removal processes.

As no emulsion or dispersion is formed in the method disclosed, the resultant formulation is substantially devoid of particles and is a true solution. In case particles are present, such particles will have an average particle size below 100 nm, alternatively below 50 nm, alternatively below 20 nm and can be termed an essentially particle free oily solution. This process is advantageous in contrast to other methods known in the art, which comprise a step of emulsification and/or dispersion. Known methods involving emulsification or dispersion result in the formation of particle containing compositions as exemplified below.

It was surprisingly found that the formulation of the present invention can be subject to sterilization such as but not limited to autoclaving without damaging the activity or the consistency of the formulation. This is in contrast to prior art formulations generated through a method of preparation involving emulsification or nanodispersion, which is subsequently lyophilized to obtain an anhydrous gel. Autoclaving the prior art formulations will destroy the nanoparticles present in the gel and in effect the activity and consistency of the formulation.

Pro-Liposomal, Non-Mucous Stock Formulations

The invention is based, in part, on the surprising discovery that a ready-to-use stock formulation, into which a local anesthetic is easily mixed, can be formed. The stock formulation comprises a natural non-synthetic phospholipid; a non-aqueous pharmaceutically acceptable carrier; and a co-solvent as a viscosity regulator. According to some embodiments, the stock formulation is devoid of water except for residual moisture that may be present in the excipients used to make the composition. In specific embodiments the residual moisture was below 0.3% as determined using the Karl Fischer method for automatically determination of water content. In specific embodiments the residual moisture was below 0.15% as determined using the Karl Fischer method for automatically determination of water content.

Upon preparation of the stock formulation, the local anesthetic can readily be added without further processing of the formulation. Alternatively, the local anesthetic is pre-dissolved prior to being added to the stock formulation. According to some embodiments, the local anesthetic is dissolved in the same or a different pharmaceutically acceptable non-aqueous carrier prior to being added to the stock formulation. Alternatively, the local anesthetic can be added followed by heating and mixing of the final composition.

In some embodiments, the stock formulation is devoid of particles above 100 nm. In some embodiments, the stock formulation is devoid of particles above 50 nm in size. In some embodiments, the stock formulation is devoid of particles above 20 nm in size. In some embodiments, the stock formulation is devoid of particles above 10 nm in size. In some embodiments the stock formulation is an essentially particle-free oily solution. In some embodiments the stock formulation is a clear solution.

Prior art formulations disclosed as anhydrous one phase gels (US 2012/0316108) appear as translucent suspensions of nanoparticles, but are not in fact true solutions. Prior art formulations prepared by a) mixing the components to form a primary dispersion comprising one or more phospholipid(s), and excessive water; b) homogenizing the primary dispersion to form a nanodispersion with an average particle size of less than about 200 nm in diameter c) passing the nanodispersion through a 0.2- or 0.45-micron filter; and d) removing water to less than 5%, preferably less than 3% and more preferably less than 1% by wt fail to form clear solutions and contain particles. In other words these are nanodispersions rather than clear solutions.

According to some embodiments the formulation is devoid of sugars such as but not limited to sucrose, dextrose, lactose, glucose, trehalose, maltose, mannitol, sorbitol, glycerol, amylose, starch, amylopectin, or a mixture thereof.

In one embodiment, the natural non-synthetic phospholipid can be any of the phospholipids described above. In another embodiment, the natural non-synthetic phospholipid is present in the formulation in the amount of about 10% to about 80% by weight. In yet another embodiment, the phospholipid is not a synthetic lipid such as 1,2-dimyristoyl-sn-glycero-3-phosphoglycerol (DMPG) or a pharmaceutically acceptable salt thereof. In yet another embodiment, the formulation of the invention is devoid of 1,2-dimyristoyl-sn-glycero-3-phosphoglycerol (DMPG) or a pharmaceutically acceptable salt thereof. In yet another embodiment, the compositions of the invention are substantially devoid of DMPG. In this context devoid of DMPG refers to a concentration below 0.5%, preferably below 0.1%.

In one embodiment, the first phospholipid is present in the formulation in the amount of about 40% to about 60% by weight. In another embodiment, the phospholipid is phosphatidylcholine (PC) or a pharmaceutically acceptable salt thereof.

In one embodiment, the non-aqueous pharmaceutically acceptable carrier is present in the formulation in the amount of about 20% to about 50% by weight. In another embodiment, the non-aqueous pharmaceutically acceptable carrier is castor oil, sesame oil, cottonseed oil, safflower oil, or one or more triglycerides. In yet another embodiment, the ratio between the phospholipids and the non-aqueous carrier is in a range of 3:1-1:2, 2.5:1-1:5:, 2.2:1-1:1.2, 2:1-1:1. Each possibility is a separate embodiment of the invention.

In one embodiment, the co-solvent is an alcohol. In another embodiment, the alcohol is ethanol. Ethanol can be present in the formulations in the amount of about 1% to about 15% by weight. As explained above, the co-solvent can serve as a viscosity regulator. In some embodiments the viscosity of the stock formulation is below 2500 cP. In some embodiments the viscosity of the stock formulation is below 2000 cP. In some embodiments the viscosity of the stock formulation is in the range of 1000-2500 cP. In some embodiments, the viscosity of the stock formulation is in the range of 1000-2000 cP.

The non-aqueous pro-liposomal depot formulations optionally comprise an anti-oxidant. Suitable anti-oxidants have been described above.

The non-aqueous non-liposomal depot formulations can optionally comprise additional ingredients, such as various excipients, pH modifying agents, metal chelators such as EDTA or edetic acid, salts, coloring agents and the like.

While the pro-liposomal, non-aqueous depot formulation described herein are termed non-aqueous (or essentially devoid of water), residual or trace water molecules, e.g., from ingredients used to make the formulation, may remain present. Such depot formulation is still deemed to be non-aqueous. In specific embodiments the residual moisture was below 0.3%. In specific embodiments the residual moisture was below 0.15%.

Methods for Making Non-Liposomal Non-Aqueous Stock Formulations

According to some embodiments, the pro-liposomal non-aqueous pharmaceutical compositions of the invention were prepared by adding a local anesthetic to a pre-prepared stock formulation. Using this method there is advantageously no need for adding excess ethanol and subsequent evaporation of the ethanol in presence of the local anesthetic.

It was surprisingly found that a combination of heat, torque and high shear mixing resulted in the complete dissolving of the phospholipid in the pharmaceutically acceptable non-aqueous carrier.

The stock formulation was prepared as follows.
1. A pharmaceutically acceptable, non-aqueous carrier (e.g., castor oil), and optionally a co-solvent (such as an alcohol e.g., ethanol) optionally containing an anti-oxidant (e.g., cysteine HCl) is equilibrated at 65° C.
2. A natural non-synthetic phospholipid (lecithin e.g., Phospholipon® 90G) is added and high torque and shear mixed at 65° C.
3. Upon complete dissolving of the non-synthetic phospholipid the mixture is cooled to room temperature.
4. Optionally, the product of step 3 is transferred to vials and/or sterilized (e.g., by autoclaving).

A local anesthetic (e.g., ropivacaine), can now be added to the pre-prepared stock formulation. Alternatively, the local anesthetic can be added at step 1 of the method, at step 2 of the method, at step 3 of the method or at step 4 of the method. Each possibility is a separate embodiment of the invention.

As understood by the skilled in the art, the improved process of preparation eliminates the need for adding excess ethanol in the dissolution process. As a result, the subsequent removal of excess ethanol from the formulation by evaporation in presence of the local anesthetic is avoided.

It was surprisingly found that the formulation of the present invention can be subject to sterilization such as but not limited to autoclaving without damaging the activity or the consistency of the formulation. This is in contrast to similar formulations generated through a method of preparation involving generating a nanodispersion which is subsequently lyophilized to obtain an anhydrous gel. Autoclaving the latter will destroy the nanoparticles present in the gel an in effect the activity and consistency of the formulation.

Treatments of the Invention Including the Treatment of Pain

The compositions described herein are useful for carrying a local anesthetic and releasing it slowly (extended release). Thus, in some embodiments, the compositions described herein are useful for treating or relieving pain, including post-surgical (post-operative) pain. In a specific embodiment, the pain is post-operative pain.

The depot formulations described herein can be used for a variety of therapeutic purposes that require a slow release formulation.

Subjects suffering from or susceptible to pain can benefit from alleviation of pain according to the methods described herein for a longer period of time. In one embodiment, administration of a local anesthetic depot formulation can be sustained for several hours, e.g., 12 hours to 24 hours, 24 hours to 48 hours, 48 hours to 72 hours, or more. If longer period of pain relief is desired, the administration of the local anesthetic depot formulation can be repeated. Typically, administration of the depot formulation can be repeated two, three or more times within a period ranging from about 1 week to about 12 months or more. In one embodiment, a local anesthetic may be administered to an individual for a period of, for example, from about 2 hours to about 72 hours, from about 4 hours to about 36 hours, from about 12 hours to about 24 hours, from about 2 days to about 5 days, or other ranges or time, including incremental ranges with these ranges, as needed.

This extended period of drug delivery of the invention is made possible by the onetime injection with relatively high concentration of the local anesthetic present in the depot formulations described herein, without the hazard of bursting effect, a sudden increase of dose to toxic levels or levels which may affect the CNS or Cardiovascular system. In particular embodiments, a local anesthetic is delivered to the subject without the need for re-accessing the syringe and/or without the need for re-filling the syringe or repeated dosing after a period of time.

The actual dose of drug delivered, can be readily calculated by one of skill in the art and will vary with a variety of factors such as the potency and other properties of the selected drug used (e.g., hydrophobicity).

According to some embodiments substantially continuous delivery of a local anesthetic (e.g., by infusion, diffusion, etc.) can be accomplished using, for example, a drug delivery device in the form of an external or implantable pump. Routes of delivery contemplated by the invention include, but are not necessarily limited to, implants, parenteral routes (e.g., subcutaneous injection infiltration or instillation, intravenous, intramuscular, intraspinal, infiltration and the like) as well as topical application. Each possibility is a separate embodiment of the invention. Parenteral delivery into an open wound or next to it (e.g., infiltration into a surgical incision) is a delivery route of particular interest.

Pain Susceptible to Management with Local Anesthetics

In one embodiment, administration of a local anesthetic depot formulation described herein can be used to facilitate management of pain that is associated with any of a wide variety of disorders, conditions, or diseases. Causes of pain may be identifiable or unidentifiable. Where identifiable, the origin of pain may be, for example, of malignant, non-malignant, infectious, non-infectious, or autoimmune origin.

Subjects who are not presently suffering from a disease or condition, but who are susceptible to such may also benefit from prophylactic pain management using the devices and methods of the invention, e.g., prior to traumatic surgery. Pain amenable to therapy according to the invention may involve prolonged episodes of pain alternating with pain-free intervals, or substantially unremitting pain that varies in severity.

In general, pain can be somatogenic, neurogenic, or psychogenic. Somatogenic pain can be muscular or skeletal (i.e., osteoarthritis, lumbosacral back pain, posttraumatic, myofascial), visceral (i.e., chronic pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes, toxicity, etc.), and can be related to nerve entrapment, facial neuralgia, perineal neuralgia, post-amputation, thalamic, causalgia, and reflex sympathetic dystrophy. Each possibility is a separate embodiment of the invention.

Specific examples of conditions, diseases, disorders, and origins of pain amenable to management include, but are not limited to, post-operative pain (also referred to as post-surgical pain), cancer pain (e.g., metastatic or non-metastatic cancer), chronic inflammatory disease pain, neuropathic pain, iatrogenic pain (e.g., pain following invasive procedures or high dose radiation therapy, e.g., involving scar tissue formation resulting in a debilitating compromise of freedom of motion and substantial chronic pain), complex regional pain syndromes, failed-back pain (chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), chronic headaches (e.g., migrans), causalgia, hyperesthesia, sympathetic dystrophy, phantom limb syndrome, denervation, and the like. Pain can be associated with any portion(s) of the body, e.g., the musculoskeletal system, visceral organs, skin, nervous system, etc. Each possibility is a separate embodiment of the invention.

Cancer pain is an example of one broad category of pain that may be alleviated using the depot formulations of local anesthetic. One of the underlying causes of cancer pain is the severe local stretching of tissues by the neoplastic lesion. For example, as the cancer cells proliferate in an unrestricted manner, the tissues in the local region of cancer cell proliferation are subjected to mechanical stress required to displace tissue and accommodate the increased volume occupied by the tumor mass. When the tumor burden is confined to a small enclosed compartment, such as the marrow of a bone, the resulting pressure can result in severe pain. Another cause of pain can result from the aggressive therapies used to combat the patient's cancer, e.g., radiation therapy, chemotherapy, etc. Such cancer therapies can involve localized or widespread tissue damage, resulting in pain.

Pain associated with any type of malignant or non-malignant cancer may be amenable to alleviation according to the methods described herein. Specific examples of cancers that can be associated with pain (due to the nature of the cancer itself or therapy to treat the cancer) include, but are not necessarily limited to lung cancer, bladder cancer, melanoma, bone cancer, multiple myeloma, brain cancer, non-Hodgkin's lymphoma, breast cancer, oral cancers, cervical cancer, ovarian cancer, colon cancer, rectal cancer, pancreatic cancer, dysplastic nevi, endocrine cancer, prostate cancer, head and neck cancers, sarcoma, Hodgkin's disease, skin cancer, kidney cancer, stomach cancer, leukemia, testicular cancer, liver cancer, uterine cancer, and aplastic anemia. Certain types of neuropathic pain can also be amenable to treatment according to the invention.

Chronic back pain, which may also be amenable to management using the methods described herein, is another broad category of pain. Chronic back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease.

Administration of Pro-Liposomal Non-Aqueous Depot Formulations

It is anticipated that the pain relief using the depot formulations of local anesthetics, such as but not limited to ropivacaine, will be sustained for a period of at least 2-3 days and be sufficient to reduce or eliminate the need for systemic analgesics or patient self-controlled analgesia. In some embodiments, the depot formulations of a local anesthetic, such as ropivacaine, is designed to replace or augment existing post-surgical pain products.

The amount of the local anesthetic that is effective in the treatment or prevention of a pain can be determined by standard clinical techniques. In addition, in vitro or in vivo assays can optionally be employed to help identify optimal dosage ranges. The precise dose to be employed can also depend on the route of administration, and the seriousness of the pain being treated and can be decided according to the judgment of the practitioner and each subject's circumstances in view of, e.g., published clinical studies. Suitable effective dosage amounts, however, range from about 0.1% to about 10% by weight of the depot formulation. In some embodiments the effective dosage is about 0.2%, 0.5%, about 1%, about 1.5%, about 2%, about 2.5%, about 3%, about 3.5% mg, about 4%, about 4.5%, about 5%, about 6% mg, about 7%, about 8%, about 9%, or about 10%.

Equivalent dosages can be administered over various time periods including, but not limited to, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one local anesthetic is administered, the effective dosage amounts correspond to the total amount administered.

The dosage regimen utilizing the depot formulations of local anesthetics described herein can be selected in accordance with a variety of factors including type, age, weight, sex and medical condition of the subject; the severity of the condition to be treated; the route of administration; the renal or hepatic function of the subject; and the particular local anesthetic employed. A person skilled in the art can readily determine the effective amount of the local anesthetic useful for treating pain, including the specific type of pain to be treated.

The depot formulations of a local anesthetic can be administered in a single daily dose. Furthermore, the depot formulations can be administered parenterally, by implantation, topically, or in the form of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of local anesthetic ranges from about 0.1% to about 10%, (w/w) or (w/v).

The depot formulations can be assayed in vitro or in vivo for the desired therapeutic or prophylactic activity prior to use in humans. Animal model systems can be used to demonstrate safety and efficacy of the depot formulations described herein.

The present methods for treating or preventing pain in a subject in need thereof can further comprise administering another prophylactic or therapeutic agent to the subject being administered the local anesthetic. In some embodiments the other prophylactic or therapeutic agent is administered in an effective amount. The other prophylactic or therapeutic agent includes, but is not limited to, an anti-inflammatory agent, an anti-renal failure agent, and anti-cardiovascular disease agent, an antiemetic agent an anxiolytic agent, and an analgesic agent.

In some embodiments, the other prophylactic or therapeutic agent is an agent useful for reducing any potential side effect of the local anesthetic. Such potential side effects include, but are not limited to, nausea, vomiting, headache, low white blood cell count, low red blood cell count, low platelet count, headache, fever, lethargy, a muscle ache, general pain, bone pain, pain at an injection site, diarrhea, neuropathy, pruritus, a mouth sore, alopecia, anxiety or depression. Each possibility is a separate embodiment of the invention.

In some embodiments, the depot formulation of a local anesthetic can be administered prior to, concurrently with, or after surgery, or on the same day, or within 1 hour, 2 hours, 12 hours, 24 hours, 48 hours or 72 hours of each other. Each possibility is a separate embodiment of the invention.

In some embodiments, the depot formulation of a local anesthetic can be administered prior to, concurrently with, or after an anti-inflammatory agent, or on the same day, or within 1 hour, 2 hours, 12 hours, 24 hours, 48 hours or 72 hours of each other. Each possibility is a separate embodiment of the invention.

In some embodiments, the depot formulation of a local anesthetic can be administered prior to, concurrently with, or after an opioid or non-opioid analgesic agent, or on the same day, or within 1 hour, 2 hours, 12 hours, 24 hours, 48 hours or 72 hours of each other. Each possibility is a separate embodiment of the invention.

Effective amounts of the other prophylactic or therapeutic agents are well known to those skilled in the art. However, it is well within the skilled artisan's purview to determine the other prophylactic or therapeutic agent's optimal effective amount range. In some embodiments of the invention, where another prophylactic or therapeutic agent is administered to a subject, the effective amount of the local anesthetic in the depot formulation is less than its effective amount would be where the other prophylactic or therapeutic agent is not administered. In this case, without being bound by theory, it is believed that the local anesthetic and the other prophylactic or therapeutic agent act synergistically to treat or prevent pain.

Pharmaceutical compositions of the invention for parenteral administration comprise a product according to the invention in combination with one or more pharmaceutically acceptable sterile non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The pro-liposomal, non-aqueous depot formulations of a local anesthetic can be infiltrated or applied to the open surgical wound either topically or injected with as syringe. In some embodiments, the formulations are administered by subcutaneous (intra-dermal) injection.

Products Containing Depot Formulations Described Herein

Kits

The invention provides kits that can simplify the administration of a depot formulation of a local anesthetic to a subject.

A typical kit comprises a unit dosage form of a depot formulation of the local anesthetic. In one embodiment the unit dosage form is a container, which can be sterile, containing an effective amount of a depot formulation of the local anesthetic. The kit can further comprise a label or printed instructions instructing the use of the depot formulation of a local anesthetic to treat or prevent a pain, such as post-surgical pain.

A kit can also comprise a container containing the stock formulation of any of the above embodiments. The kit may further comprise a local anesthetic.

The kit can also comprise a prefilled syringe (with or without a needle) suitable for administration of the local anesthetic. In one embodiment the syringe includes an 18-25 G needle. In another embodiment the syringe includes a 21 G needle.

The kit can also further comprise a unit dosage form of another prophylactic or therapeutic agent, for example, a container containing an effective amount of the other prophylactic or therapeutic agent. In some embodiments the kit comprises a container containing a depot formulation of a local anesthetic and an effective amount of another prophylactic or therapeutic agent. Examples of other prophylactic or therapeutic agents include, but are not limited to, those listed above.

Pre-Filled Syringes

According to certain embodiments the invention provides a pre-filled syringe filled with a depot formulation described herein. The depot formulation includes a local anesthetic. The pre-filled syringe can also comprise a needle suitable for injection of the depot formulations or other means of deploying the formulation. In one embodiment the needle is an 18-25 G needle. In another embodiment the needle is a 21 G needle. The depot formulation of a local anesthetic is delivered through a sterile, prefilled syringe proximate to a target site such as a surgical wound.

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. A number of references have been cited, the entire disclosures of which are incorporated herein by reference in their entirety.

EXAMPLES

Example 1

Preparation of Pro-Liposomal- Non-Aqueous Oleaginous Ropivacaine Depot Formulation A pro-liposomal, non-aqueous oleaginous formulation of ropivacaine was prepared as follows. The required amount of ropivacaine HCl monohydrate was placed into a pre weight (tare) round bottom flask and the required amount of cysteine HCl is added. The required amount of lecithin (PL90G, phosphatidylcholine) was added into the flask followed by the required amount of castor oil (the order of ingredients is unimportant). Absolute ethanol, in an amount equal to or exceeding the required final amount, was added to the flask. The flask was closed tightly and weighed. The flask with ingredients was placed into a water bath sonicator and heated to about 50° C. When all ingredients were dissolved and absolute ethanol amount exceeded the required final amount, the flask was connected to a suitable evaporating apparatus (e.g., Rotavapor) and the water bath was maintained at a heat of about 50° C. Vacuum was adjusted to 200 mbar and the flask was rotated at about 60 rpm. The vacuum was gradually decreased in increments of 10 mbar until it reached 40 mbar. The evaporation is continued until the weight of the flask indicated to be containing the required final amount of 6% or less (w/w) of absolute ethanol, as calculated by weighing the flask and contents or the amount of evaporated and cooled down alcohol trapped outside the evaporator. The flask and its contents were allowed to cool to room temperature. If necessary, absolute ethanol was added to reach 6% (w/w). If the solution was determined to contain less than 6% (w/w) of absolute ethanol, ethanol was added to make up the desired percentage % (w/w). The flask may be stored refrigerated or at room temperature until the vial or syringe filling is planned. The flask is re heated and rotated in a sonicator bath heated to 50° C. for about 1 hour before dispensing to final containers. The flask and its contents are allowed to cool to room temperature. Using a suitable filling apparatus, the resultant solution is filled into glass vials or other containers.

As can be seen from the process described above, no water is added during this entire process.

Example 2

Pro-Liposomal- Non-Aqueous Oleaginous Formulations of Ropivacaine

The non-aqueous non-liposomal oleaginous ropivacaine formulation was prepared in accordance with the process described in Example 1. Table 1A provides the components of the formulation (formulation A).

TABLE 1A

| FORMULATION A | % [w/w] |
| --- | --- |
| Ropivacaine HCl monohydrate | 4.78% (equivalent to 4% ropivacaine base) |
| Phospholipon (PL90G) (Lipoid (GMbH)) (Pure phosphatidylcholine stabilized with 0.1% ascorbyl palmitate) | 53.91% |
| Castor oil | 35.21% |
| Cysteine HCl | 0.1% |
| Ethanol* | 6.0% |

*Quantity reflects the final concentration in the formulation, but used in larger quantities during the production process Table 1B provides the components of inferior formulations comprising synthetic phospholipids used for comparison with Formulation A.

TABLE 1B

| COMPONENTS | Formulation 3 | Formulation 4 |
| --- | --- | --- |
| Ropivacaine HCl monohydrate | 4.78% (equivalent to 4% ropivacaine base) | 4.78% (equivalent to 4% ropivacaine base) |
| DMPG (1,2,Dimyristoyl-sn-glycero-3-phosphoglycerol NH4/Na salt (Avanti Polar Lipids USA) | 5.02% | 5.02% |
| Phospholipon (PL90G) (Lipoid (GMbH)) (Pure phosphatidylcholine stabilized with 0.1% ascorbyl palmitate) | 48.89% | 50.89% |
| Castor oil | 35.21% | 35.21% |
| Cysteine HCl | 0.1% | 0.1% |
| Ethanol* | 6.0% | 4.0% |

*Quantity reflects the concentration in the final formulation, but used in larger quantities during the production process.

Stability testing of the samples in clear vials was performed for samples stored in stability chambers at room temperature (RT) and accelerated stability conditions at 40° C. over a period of several weeks to several months by visual observation of the samples for any precipitation, change in color, and change in clarity followed by chemical dosage confirmation. It was found that Formulations 3 and 4 precipitated at RT which rendered the formulations into virtually opaque gels. These precipitations could not be re-dispersed, even with vigorous shaking. In contrast the preferred depot formulation A was physically and chemically stable for over 24 months under these conditions. It was further noted, that formulation A was clear and transparent, with no visible particles. Thus, it was concluded that formulations containing synthetic phospholipids are unsuitable for further commercial development.

Example 3

Viscosity Measurements of the Depot Formulations

The viscosity of depot formulation A as well as formulation 3 and 4 was measured by the spindle method using viscometer (Brookfield model DV-II) equipped with spindle 5; bath temperature of 30° C., speed of 30, 60 and 100 RPM.

Formulation A has a lower viscosity (1720 cP) than formulations 3 and 4 which contain DMPG (3031 cP). This difference is made explicit by the increased flow characteristics of depot formulation A as well as an eased overall handling (syringability and injectability) which makes the formulation A more suitable for parenteral administration. Formulations devoid of ethanol had higher viscosity and are unsuitable for parental administration.

Example 4

Liposome Like Structures Formation Upon Exposure to Saline or Pig Plasma

Depot formulation A was kept in scintillation vials and 0.9% NaCl solution or pig plasma were slowly injected into the formulation up to a quantity of 50% (w/w) of the total formulation weight reaching a formulation/saline ratio of 1:1. The resulting mixtures were then agitated at 200 rpm using a water bath shaker at 37° C.

The physical characteristics of depot formulation A containing saline or pig plasma, at a ratio of 1:1, were evaluated using the following methods:
1. Particle size distribution: Particle size distribution was analyzed using the Coulter LS230 Particle Size Analyzer.
2. Cryo-TEM morphological evaluation: Morphological evaluation was performed by means of TEM (FEI Technai 12 G2 120 kV with a Gatan cryo-holder maintained at −180° C. and images were recorded on a slow scan cooled charge-coupled device CCD camera Gatan manufacturer).

The particle size distribution (FIGS. 1A and B) results indicate the formation of multi lamellar liposomal vesicles (MLV) in both mixtures. A determined mean/median particle size of about 1.4 μm was obtained with the formulation A/saline dilution, suggesting more multilamellar particles than micelle particles or oil-in-water emulsion droplets which are in the nanosize range. The determined mean/median particle size of the depot formulation A/pig plasma (1:1) was about 20 μm which is significantly larger than in the case of depot formulation A/saline (1:1), indicating MLV formation upon exposure to bodily fluids in vivo.

For the Cryo-TEM morphological evaluation, formulation A was diluted with pig plasma to reach 1:1 and 1:2 dilutions. Samples were then subjected to Cryo-TEM. Blank pig plasma was used as control.

Figure 2:
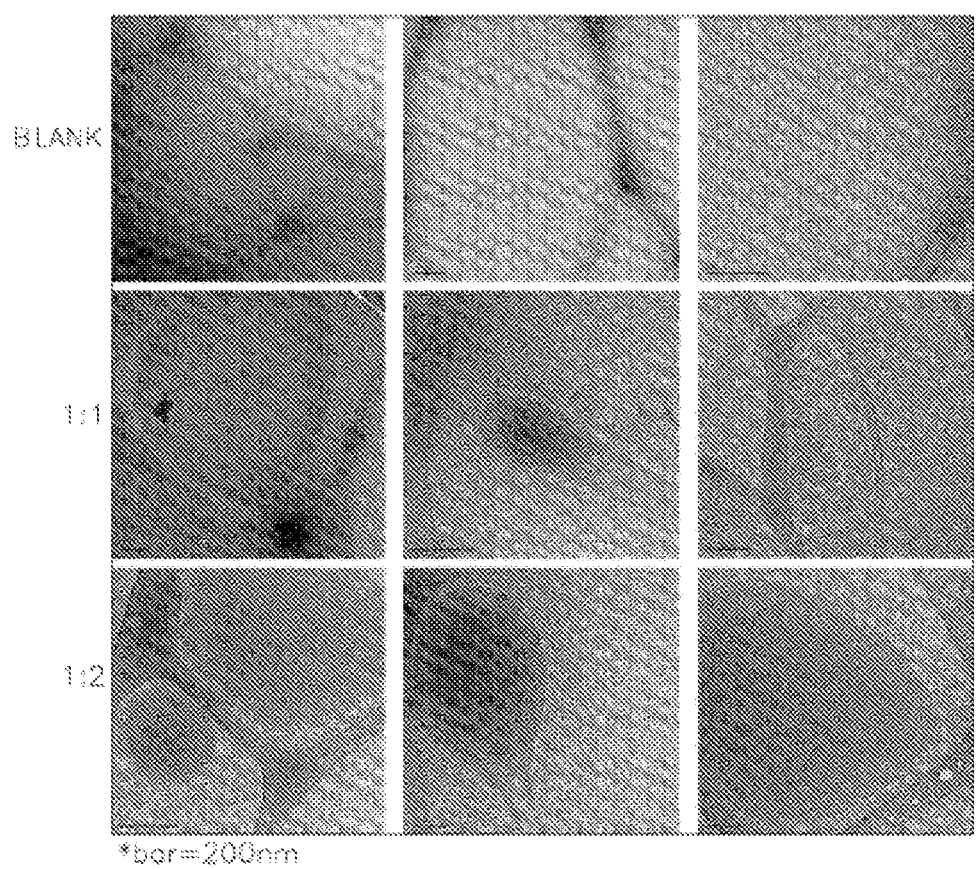
FIG. 2 represents Cryo-TEM pictures of formulation A diluted with pig plasma at ratios of 1:1 and 1:2.

As seen in FIG. 2, multilamellar vesicles and similar lipid assemblies were easily detected following 1:1 and 1:2 dilution of formulation A with pig plasma. This was in sharp contrast to the absence of such structures in the blank minipig plasma sample.

It is concluded that depot formulation A creates MLVs upon exposure to pig plasma and that the addition of the viscosity agent ethanol surprisingly does not interfere with the formation of these liposomal vesicles upon exposure to aqueous solutions. Moreover, these results indicate that the slow release and extended duration of pain relief obtained when administering formulation A of the present invention are most likely due to the formation of liposomes or other lipidic vesicular structures and do not require a gel or a gel-like consistency as generally presumed.

Example 5

In vivo efficacy of Pro-Liposomal- Non-Aqueous Oleaginous Formulations of Ropivacaine In this study, ropivacaine formulations were evaluated in the juvenile pig model for post-operative pain using Von Frey methodology. The Von Frey hair filaments are made from a nylon filament of varying diameters. The filaments are to be pressed against the skin with enough force so that the hair buckles and forms a U-shape. The gram force required for each filament to buckle is constant, i.e. these hairs can be used to apply a very accurate and repeatable force to test specific, predetermined areas on the skin, thus making the Von Frey hair a diagnostic, research and screening tool. It is readily used to study skin areas with normal responsiveness as well as hyper- or hyposensitive areas.

The various ropivacaine formulations administered to pigs are shown in Table 2. The term 4% ropivacaine refers to 4% ropivacaine base.

TABLE 2

| Group | Formulation | Total Dose of Ropivacaine (mg) Per Animal | Volume | Route |
|---|---|---|---|---|
| 1M | Positive Control Ropivacaine injectable solution 0.5% (Naropin 1% diluted 2X) | 25 mg | 5 ml | SC |
| 2M | Formulation 4 placebo 4% ethanol | | 5 ml | SC |
| 3M | Formulation 3 6% EtOH | 200 mg | 5 ml | SC |
| 4M | Formulation A 6% ethanol | 200 mg | 5 ml | SC |

\* SC is meant as being instilled into the surgical wound following suturing

Table 3 lists the experimental groups in the study. The term 4% ropivacaine refers to 4% ropivacaine base.

TABLE 3

| Group No. | No. of Animals | Treatment | Solution | Dosing | Von Frey Tests |
|---|---|---|---|---|---|
| 1M | 6 | Positive Control (Naropin ®) | commercial product | Once SC administration immediately post incision closure | Group 1M Pain assessment by Von Frey was performed prior to surgery and at 1.5 h, 3 h, 6 h, 8 h and 12 h post-surgery |
| 2M | 6 | Formulation - Placebo | 6% EtOH | | Groups 2M and 3M: Pain assessment by Von Frey was performed prior to surgery and at 3 h, 6 h, 8 h, 24 h, 30 h, 36 h. Additionally animals that demonstrate drug efficacy at 36 h, are tested again at the following time points 42 hours and 48 hours |
| 3M | 6 | Formulation 3 | 4% Ropivacaine 6% EtOH | | |
| 4M | 6 | Formulation A | 4% Ropivacaine 6% EtOH | | Group 4M: Pain assessment by Von Grey was performed prior to surgery and at 1.5 h, 3 h, 6 h, 8 h, 24 h, 30 h and 36 h. Additional tests are performed if any of the above groups show analgesia after 36 hours. |
| 5M | Sham (Negative Control) no injection made | | | | Group 5M: Pain assessment by Von Grey was performed prior to surgery and at 1.5 h, 3 h, 6 h, 8 h,, 24 h, 30 h and 36 h. Additional tests |

TABLE 3-continued

| Group No. | No. of Animals | Treatment | Solution | Dosing | Von Frey Tests |
|---|---|---|---|---|---|
| | | | | | are performed if any of the above groups show analgesia after 36 hours |

During surgery the piglets were anesthetized by an isoflurane/oxygen mixture delivered through a facemask. A 6-7 cm long skin and fascia incision was made in the left flank, keeping the muscle intact. The skin incision was closed using a sterile suture. The TI treatments, Placebo, gel test formulation (formulation 3), oily test formulation (formulation A) or positive control were carefully administered into the surgical made pocket as two 2.5 ml injections (5 ml/animal). Each injection was performed using a fresh 3.5 ml luerlock syringe through an 18G needle. Each treatment was applied in the same direction (cranial to caudal). Each incision was performed using an autoclaved sterile set of surgery tools. Following the incision the pigs optionally received 2 types of antibiotics. The animals were kept under anesthesia for the duration of the surgery and dosing (about 20 minutes).

The test formulations were administered only once on study day 0 as subcutaneous injection under the suture. The animals' baseline response to Von Frey was taken on study day −1. The data considered to serve as baseline was the data recorded on study day −1. Animals were included in the study if the flack withdrawal force at baseline was ≤26 g. Preferably, the flank withdrawal force at baseline was 60 g at both flanks. Pain is considered as flank withdrawal at a force of ≤10 g.

Von Frey filaments (Ugo Basile) were applied at approximately ~0.5 cm proximal to the incision line to the surface of the flank skin. As the gram number of filaments increased, the force on the flanks' skin increased. The maximum force was 60 g. Filaments were applied until the animal withdrew from the stimuli. Each filament was applied 3-5 times.

Figure 3:
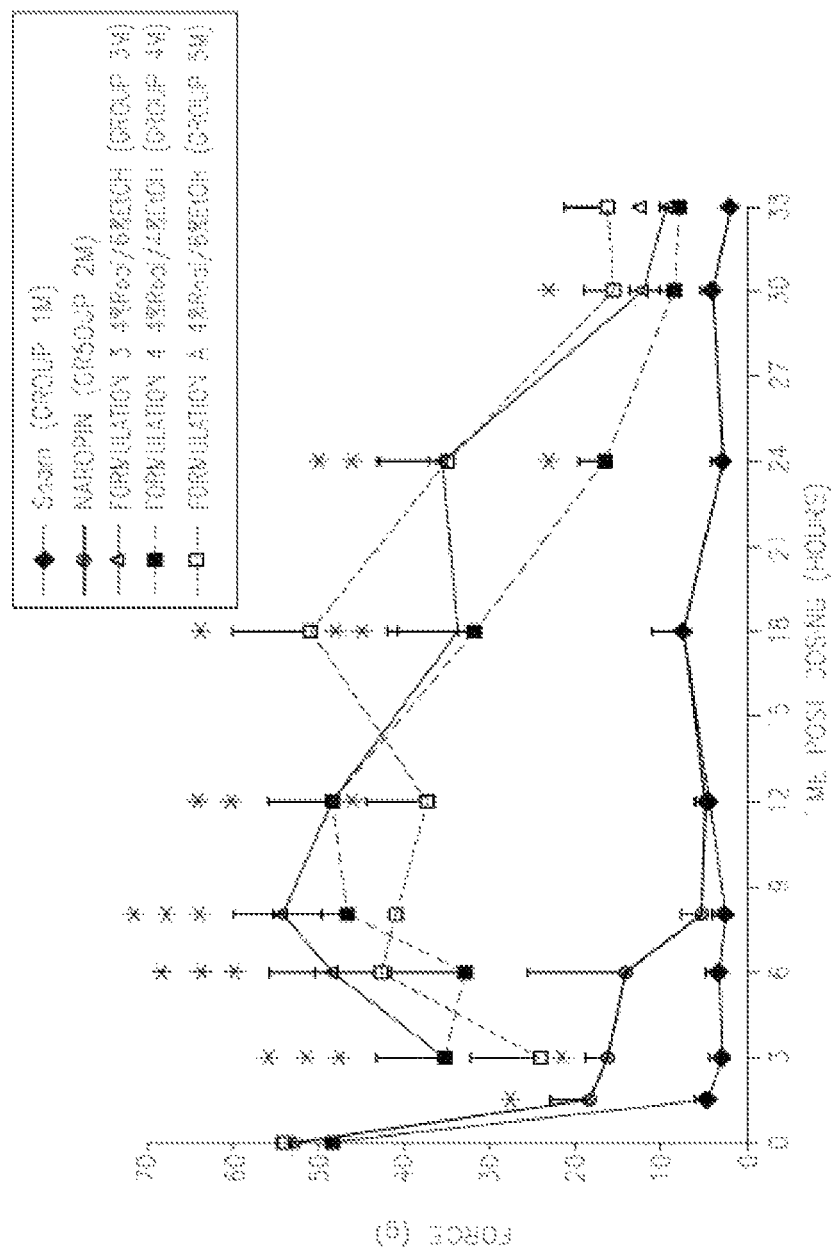
FIG. 3 is a graphical representation of a post-operative pain response study in 10 kg piglets administered with various ropivacaine formulations.

As seen in FIG. 3, formulation A, which is an oleaginous solution, unexpectedly provided a longer pain relief compared to all other formulations tested in the experiment, including the formulations having identical ethanol and ropivacaine concentrations. This is evident from the force value shown in FIG. 3 at 18 hrs post-dosing. This result is surprising because the oleaginous solution is less viscous than the gel like formulation containing DMPG. Depot formulations are commonly solid implants or gel-like substances and do not disperse or spread when injected into tissue. Accordingly, it is generally believed that more viscous formulations are retained in the tissue longer than less viscous formulations, as a more viscous material disperses more slowly if at all. It was found that when the viscosity of the formulation is in the range of 1000-2000 cP, residence time and duration of activity is optimal, despite the decreased injectability of the formulation.

The finding that a depot formulation in the form of an oleaginous solution (formulation A) provided a favorable sustained release profile was unexpected and surprising and suggested that indeed the addition of the viscosity reducing agent ethanol did not have a negative effect, namely neither on the efficacy of ropivacaine nor on the duration of the pain relief.

In order to evaluate the distribution of ropivacaine between wound tissue and blood, wound tissue and blood samples were taken 4 days after administration of either Naropin® or formulation A, and Ropivacaine concentrations were determined by using HPLC/MS/MS.

As can be seen from the results presented in Table 4, a significantly higher concentration of ropivacaine in the wound was obtained when using depot formulation A as compared to that of the Naropin® injection.

TABLE 4

| | Ropivacaine concentration (ng/mL) | |
|---|---|---|
| | Wound | Plasma |
| Formulation A* | 3798.5 | 31.4 |
| Naropin ®** | 15.4 | 2.1 |

*results shown are the mean values obtained in 6 independent measurements.
**results shown are the mean values obtained in 3 independent measurements.

These results indicate that depot formulation A enables the maintenance of higher ropivacaine concentrations in the vicinity of the wound even four days after injection.

Based on all the above results, it was concluded that the depot formulation A is superior to the Naropin® commercial formulation as well as the gel formulations and therefore this formulation was selected for further development.

Example 6

Phase I—Clinical Efficacy Study in Healthy Human Volunteers

The purpose of this study was to evaluate the onset and duration of analgesia of 2.5 ml each of depot formulation A, ropivacaine solution (Naropin®) and placebo gel formulation administered by subcutaneous (SC) injection in a human experimental pain model.

Part 1 of the study included fifteen (15) male subjects who were evaluated for 72 hours post injection. Each subject acted as his own control and received all treatments simultaneously as 2.5 mL subcutaneous injections. Table 5 describes the treatments which each patient received.

TABLE 5

| Treatment | Volume |
|---|---|
| Formulation A | 2.5 mL |
| Formulation w.o. ropivacaine placebo | 2.5 mL |
| Ripovacaine solution 0.5% (Naropin ®) | 2.5 mL |

Four circumscribed areas were marked on each volunteer's back and each of the three treatments was injected into one randomly assigned area while a fourth, randomly selected area, was used as a non-injected control. The effect of local analgesia induced by the study medication and controls were evaluated using Tactile Threshold (von Frey hair), Pinprick Test (PPT), Cold Sensation, and Heat Pain Tolerance. The tests showed that the duration of the pain relief was longer when formulation A was administered compared to the Naropin® solution. In accordance the percentage of subjects who achieved analgesia for ≥24 hours was greater following administration of formulation A, as can be seen in table 6.

TABLE 6

| Response | Formulation A | Naropin ® | Placebo formulation with out ropivacaine |
|---|---|---|---|
| Yes (%) | 53.8 | 30.8 | 7.7 |

Part 2 of the study was a pharmacokinetic analysis to which nine subjects were enrolled. Each subject received a 2.5 mL subcutaneous single injection on his back of either oligoneous depot formulation A (6 subjects) or Ropivacaine Injectable commercial Solution 0.5% (Naropin) (3 subjects). Venous blood samples (9 ml samples), for the measurement of plasma concentration of ropivacaine, were drawn immediately before the drug administration (time 0) and at 0.5, 1, 1.5, 2, 3, 6, 9, 12, 18, 24, 30, 36, 48, and 72 hours after drug administration.

Figure 4:
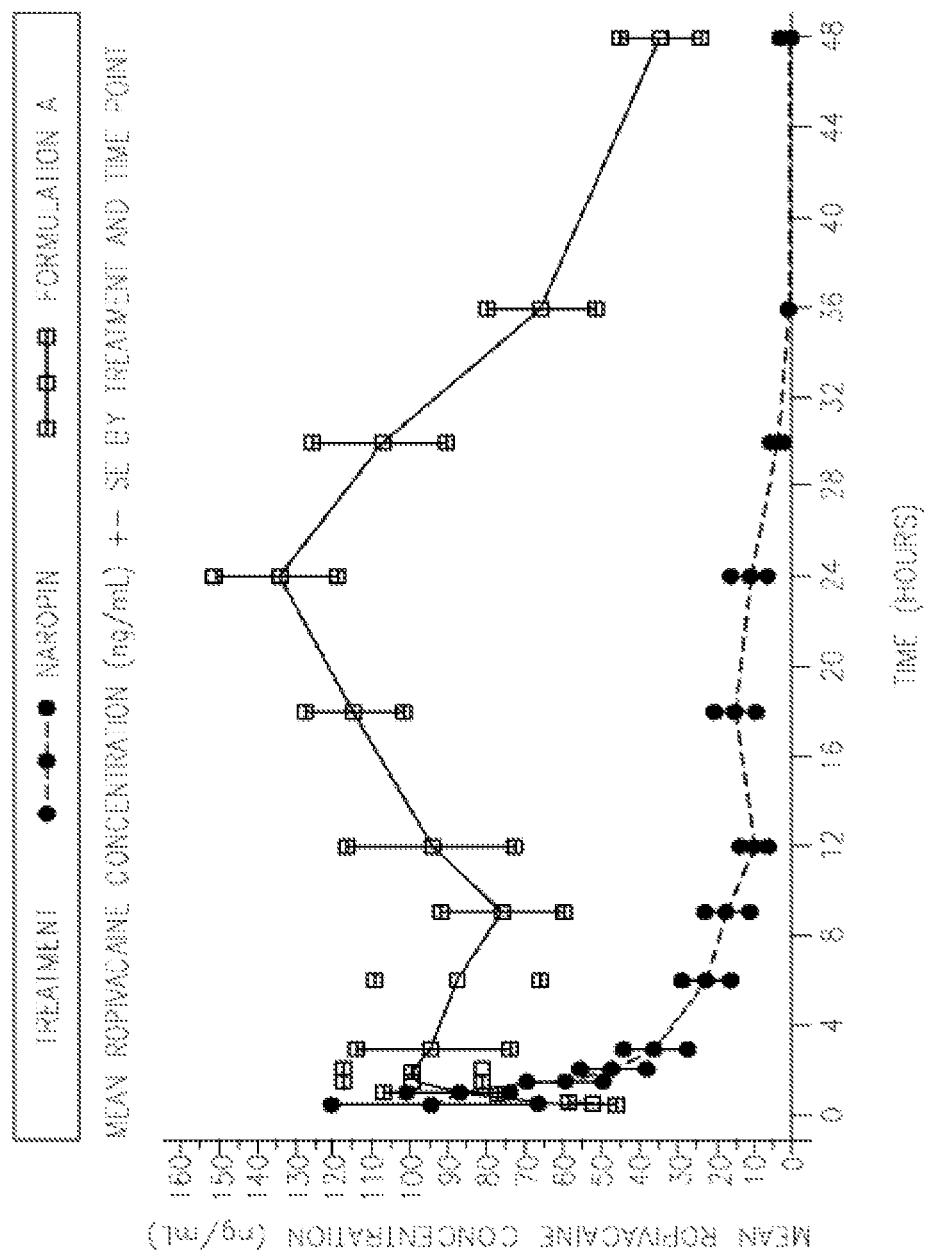
FIG. 4 is a graphical representation of pharmacokinetic response study in healthy volunteers administered with various ropivacaine formulations.

As seen in FIG. 4, the concentration of ropivacaine in the blood was significantly higher when formulation A was administered, compared to Naropin®, already 3 hours after injection. The duration of the effects for formulation A lasted for over 48 hours and was significantly longer than the ropivacaine solution (Naropin®) which lasted only for up to 12 hours. Table 7 summarizes the main pharmacokinetic parameters. As seen in the table, the Cmax value of formulation A resembles that of the Naropin® injection and is distinguishably below the toxic threshold of 0.6 mg/mL and distinguishably below the Cmax of approximately 0.87 mg/mL obtained for lysosomal formulations of ropivacaine, indicating that an initial burst of ropivacaine is avoided. This facilitates administration of high ropivacaine concentration in a single injection.

TABLE 7

| Parameter | Naropin ® N = 3 | Formulation A N = 6 | P value* |
|---|---|---|---|
| Cmax (ng/mL) | 100.02 ± 41.34 | 164.35 ± 42.95 | 0.1934 |
| Tmax (hr) | 0.83 ± 0.29 | 15.25 ± 10.83 | 0.0586 |
| AUClast (ng · hr/mL) | 596.69 ± 147.78 | 4669.04 ± 1242.98 | 0.0595 |
| AUCinf (ng · hr/mL) | 614.00 ± 138.33 | 5032.39 ± 1502.73 | 0.0595 |
| Lambda-z (1/hr) | 0.12 ± 0.08 | 0.05 ± 0.02 | |
| Number of points for Lambda-z | 6.67 ± 5.51 | 4.67 ± 1.63 | |
| T½ (hr) | 9.55 ± 8.86 | 15.43 ± 7.33 | 0.3926 |
| Volume (mL) | 297379.07 ± 277334.00 | 449449.02 ± 163865.10 | |
| Clearance (mL/hr) | 21029.41 ± 4498.87 | 21417.55 ± 6326.11 | |

The conclusion of this study was that formulation A has a favorable prolonged release profile compared to the commercially available 0.5% ropivacaine solution, and that the safety of formulation A was not compromised.

Example 7

Preparation of a Pro-Liposomal- Non-Aqueous Oleaginous Stock Depot Formulation

It was advantageously found that a pro-liposomal non-aqueous ready to use depot formulation which does not require evaporation of the ethanol in presence of the local anesthetic can be prepared. The combination of heat, torque and high shear mixing enabled preparing a ready-to-use stock formulation that is stable, does not contain excess ethanol and facilitates adding the local anesthetic required.

The stock formulation was prepared as follows:

The required amounts of castor oil, ethanol and cysteine (pre-dissolved in the ethanol) were added to a container and equilibrated at 65° C. The lecithin was then added followed by high torque and shear mixing at 125 rpm and 3577 rpm respectively for approximately half an hour. Following complete dissolving of the lecithin the mixture was discharged into flasks and stored over-night yielding transparent oils. As understood from the process described, no water was added during this entire process.

It is understood by the skilled in the art that the stock formulation of the invention facilitates the addition of various local anesthetics.

It is further understood that the improved process of preparation eliminates the need for adding excess ethanol in the dissolution process. As a result, the subsequent removal of excess ethanol from the formulation by evaporation in presence of the local anesthetic is avoided.

Table 8 provides the components of the stock formulation.

TABLE 8

| STOCK FORMULATION | % [w/w] |
|---|---|
| Phospholipon (PL90G) (Lipoid (GMbH)) (Pure phosphatidylcholine stabilized with 0.1% ascorbyl palmitate) | 56.62 |
| Castor oil | 36.98 |
| Cysteine HCl | 0.10 |
| Ethanol* | 6.30 |
| TOTAL | 100 |

Example 8

Pro-Liposomal- Non-Aqueous Oleaginous Formulations of Ropivacaine

A non-aqueous pro-liposomal oleaginous stock formulation was prepared in accordance with the process described in Example 7. Ropivacaine was added to the ready-to-use stock formulation.

Table 9 provides the constituents of compositions with various amounts of ropivacaine-HCL.

TABLE 9

| ROPIVACAINE FORMULATION (% w/w) | | | |
|---|---|---|---|
| Ropivacaine | 1.20 | 2.40 | 4.78 |
| PL90G | 55.94 | 55.26 | 53.91 |
| Castor oil | 36.54 | 36.09 | 35.21 |

TABLE 9-continued

| ROPIVACAINE FORMULATION (% w/w) | | | |
|---|---|---|---|
| Cysteine HCl | 0.10 | 0.10 | 0.10 |
| EtOH | 6.22 | 6.15 | 6.00 |
| TOTAL | 100.0 | 100.0 | 100.0 |

The final formulation was clear and transparent, with no visible particles. The final formulation was stable for at least one month under accelerated stability testing. Preferably the formulation is stable for over 2 months, over 4 months, over 6 months or longer.

Example 9

Viscosity Measurements of Ropivacaine Compositions with Different Concentrations of Co-solvent.

The viscosity of depot ropivacaine formulations with various amount of ethanol was measured by the spindle method using viscometer (Brookfield model DV-II) equipped with spindle 5; bath temperature of 30° C., speed of 30, 60 and 100 RPM. As seen from table 10, the viscosity testing demonstrated a decreased viscosity with increased ethanol concentrations.

TABLE 10

| Formulation | Speed (rpm) | | |
|---|---|---|---|
| description | 50 | 60 | 100 |
| 2% Ropi/4% EtOH | 3791 | 3779 | 3863 |
| 2% Ropi/4% EtOH | 3479 | 3439 | 3395 |
| 2% Ropi/5% EtOH | 2184 | 2280 | 2280 |
| 2% Ropi/6% EtOH | 1512 | 1620 | 1692 |
| 2% Ropi/6% EtOH | 1824 | 1760 | 1704 |

Example 10

Syringability Testing Measurements of Ropivacaine Depot Formulations with Different Concentrations of Co-solvent.

The injectability of depot Ropivacaine compositions with various amount of ethanol was measured by extrusion from a 21G syringe of a predetermined amount of the composition onto a pre-weighed dish.

As seen from table 11, the injectability rate increased with increased ethanol concentrations.

TABLE 11

| Formulation description | Injectability rate (mg/sec) |
|---|---|
| 2% Ropi/4% EtOH | 1.46 |
| 2% Ropi/4.5% EtOH | 1.76 |
| 2% Ropi/5% EtOH | 2.18 |
| 2% Ropi/5.5% EtOH | 2.38 |

Example 11

Particle Size Distribution of Depot Formulations

The particle size distribution of the depot formulation devoid of the local anesthetics prepared as described in example 7 is measured by dynamic light scattering using a Malvern Zetasizer, Coulter N4plus or Nicomp 300 particle size analyzer able to measure particle size in the submicron range (test range ≥0.5 nm≤1 μm).

Similarly, the particle size of a prior art formulation, designated herein formulation 5 (see US 2012/0316108) is also measured for comparative purposes. The comparative formulation 5 is prepared according to a method of preparation comprising the steps of a) mixing the components to form a primary dispersion comprising one or more phospholipid(s), and excessive water; b) homogenizing the primary dispersion to form a nanodispersion with an average particle size of less than about 200 nm in diameter c) passing the nanodispersion through a 0.2- or 0.45-micron filter; and d) removing water to less than 5%, preferably less than 3% and more preferably less than 1% by wt. Table 12 provides the components of prior art formulation 5.

TABLE 12

| Formulation 5 Composition (% wt) | |
|---|---|
| Component | % wt |
| Soy lecithin | 45 |
| Sesame oil | 44 |
| EDTA disodium dehydrate | 0.10 |
| Potassium monobasic phosphate | 0.14 |
| Benzyl alcohol | 1.0 |
| Ethanol | 4.0 |
| 1N KOH | pH to 7.0 |

Prior art formulation 5 is prepared as follows:
1. Weigh out sesame oil, soy lecithin and benzyl alcohol into a glass flask.
2. Add ethanol USP 200 proof and rotate the flask to dissolve all.
3. Vacuum dry to remove ethanol to less than 1% by weight.
4. Add $KH_2PO_4$, EDTA and DI-water.
5. Homogenize to form a nanodispersion.
6. Adjust pH to 7.0+/−0.2 using NaOH/HCl.
7. Sterile filter the nanodispersion through a 0.2 micrometer pore filter.
8. Lyophilize the nanodispersion to remove water to less than 2%.
9. Add ethanol.
10. Mix to obtain an anhydrous gel.

Example 12

In vivo Efficacy of Pro-Liposomal- Non-Aqueous Oleaginous Formulations of Ropivacaine as Compared to Prior Art Formulations.

The distribution of ropivacaine between wound tissue and blood is compared for different formulations. Naropin®, formulation A, or formulation 5 containing ropivacaine prepared according to a method described in Example 11 are instilled into a surgical wound only once on day 0. Wound tissue or exudate and blood samples are taken daily for up to 4 days after administration. The concentrations are determined by using HPLC/MS/MS as described in Example 4.

What is claimed is:
1. A method of treating or relieving pain in a subject in need thereof comprising administering to the subject an effective amount of a pro-liposomal non aqueous pharmaceutical composition comprising:
   a local anesthetic or pharmaceutically acceptable salt thereof;
   a naturally occurring phospholipid;
   a non-aqueous pharmaceutically acceptable carrier; and
   a viscosity regulator, wherein said composition is in the form of a clear solution, devoid of particles above 100 nm in size, stable at ambient temperature, has a viscosity below 2500 cP and substantially devoid of water, and the ratio between the phospholipids and the non-aqueous carrier is 3:1 to 1:1.

2. The method of claim 1, wherein the pain is selected from the group consisting of somatogenic, neurogenic, and psychogenic pain.

3. The method of claim 1, wherein the pain is post-operative pain or cancer pain.

4. The method of claim 1, where administering the composition provides pain relief for at least 48 hours.

5. The method of claim 1, where administering the composition provides pain relief for at least 24 hours.

6. The method of claim 1, wherein the administering comprises parenteral and topical administration of the composition.

7. The method of claim 1, wherein the non aqueous pharmaceutical composition has a viscosity below 2000 cP.

8. The method of claim 1, wherein the non aqueous pharmaceutical composition has a viscosity in the range of 1000-2000 cP.

9. The method of claim 1, wherein the non aqueous pharmaceutical composition is devoid of particles above 50 nm in size.

10. The method of claim 1, wherein said non aqueous pharmaceutical composition forms liposomes in vivo upon exposure to bodily fluids.

11. The method of claim 1, wherein the viscosity regulator is ethanol.

12. The method of claim 1, wherein ethanol is present in the amount of about 1% to about 15% by weight.

13. The method of claim 1, wherein said local anesthetic is ropivacaine.

14. The method of claim 1, wherein said local anesthetic is present in the amount equivalent to about 0.2% to about 12% by weight.

15. The method of claim 13, wherein said local anesthetic is present in the amount equivalent to about 3% to about 6% by weight.

16. The method of claim 1, wherein the naturally occurring phospholipid is present in the amount of about 40% to about 60% by weight.

17. The method of claim 1, wherein the naturally occurring phospholipid is phosphatidylcholine (PC) or a pharmaceutically acceptable salt thereof.

18. The method of claim 1, wherein the non-aqueous pharmaceutically acceptable carrier is selected from the group consisting of castor oil, sesame oil, cottonseed oil, and safflower oil.

19. The method of claim 1, wherein the non-aqueous pharmaceutically acceptable carrier is castor oil.

20. The method of claim 1, wherein the non-aqueous pharmaceutically acceptable carrier is present in the amount of about 30% to about 50% by weight.

21. The method of claim 1, wherein the non aqueous pharmaceutical composition further comprises an anti-oxidant.

22. The method of claim 1, wherein the anti-oxidant is cysteine or a pharmaceutically acceptable salt thereof.

23. The method of claim 1, wherein the pro-liposomal non aqueous pharmaceutical composition comprises:
   a local anesthetic or pharmaceutically acceptable salt thereof;
   about 40% to about 60% by weight of a naturally occurring phospholipid;
   about 30% to about 50% by weight of a non-aqueous pharmaceutically acceptable carrier selected from the group consisting of sesame oil, cottonseed oil, safflower oil and castor oil; and
   about 0.5% to about 15% by weight of ethanol as a viscosity regulator.

24. A method of treating or relieving pain in a subject in need thereof comprising administering to the subject an effective amount of a pro-liposomal non aqueous pharmaceutical composition consisting essentially of:
   a local anesthetic or pharmaceutically acceptable salt thereof;
   a naturally occurring phospholipid;
   a non-aqueous pharmaceutically acceptable carrier;
   a viscosity regulator; and
   an anti-oxidant,
   wherein said composition is in the form of a clear solution, devoid of particles above 100 nm in size, stable at ambient temperature, has a viscosity below 2500 cP and substantially devoid of water, and the ratio between the phospholipids and the non-aqueous carrier is 3:1 to 1:1.

* * * * *